United States Patent [19]

Billington et al.

[11] Patent Number: 5,595,976

[45] Date of Patent: Jan. 21, 1997

[54] TETRAHYDROPYRAN COMPOUNDS

[75] Inventors: David Billington, West Midlands, United Kingdom; Gilbert Dorey, Chaville, France; Pascale Leon, Guyllancourt, France; Ghanem Atassi, Saint Cloud, France; Alain Pierre, Les Alluets-le-Roi, France; Michael Burbridge, Courbevoie, France; Nicolas Guilbaud, Paris, France

[73] Assignee: Adir et Compagnie, Courbevoie, France

[21] Appl. No.: 521,189

[22] Filed: Aug. 30, 1995

[30] Foreign Application Priority Data

Aug. 30, 1994 [FR] France .................. 94 10462

[51] Int. Cl.⁶ .................. A61K 37/00; C07H 3/00
[52] U.S. Cl. .................. 514/25; 536/4.1; 536/17.2; 536/17.3; 536/18.1; 514/23
[58] Field of Search .................. 536/18.1, 4.1, 536/17.2, 17.3, 12.1; 514/25, 23

[56] References Cited

U.S. PATENT DOCUMENTS 4,017,608 4/1977 Gordon .................. 536/17.9

Primary Examiner—Elli Peselev
Attorney, Agent, or Firm—The Firm of Gordon W. Hueschen

[57] ABSTRACT

A compound selected from those of formula (I):

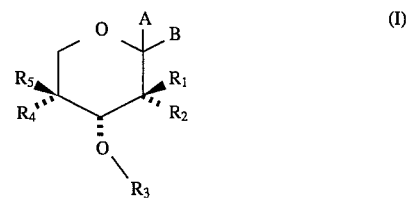

in which:

A either represents —$OR_6$, and B represents —$CH_2$—X, or, together with B and the carbon atom carrying them, forms an oxygen-containing heterocycle selected from oxirane, 2,2-dimethyl[1,3]dioxolane and [1,3]dioxolan-2-one, and $R_1$, $R_2$, $R_3$, $R_4$, $R_5$, $R_6$ and X are as defined in the description.

15 Claims, No Drawings

TETRAHYDROPYRAN COMPOUNDS

The present invention relates to new glucidic compounds having a tetrahydropyran structure, to a process for the preparation thereof, and to pharmaceutical compositions containing them. The compounds of the present invention are highly valuable for therapeutic use on account of their angiogenesis-inhibiting ability.

Angiogenesis (or neovascularisation) is defined as the development and growth of new capillary blood vessels. The process of angiogenesis is essential in many physiological situations including the development of the embryo, the normal healing of injuries and the development of the endometrium after menstruation. Apart from those situations, angiogenesis in normal adults is very rare and the mitosis of the endothelial cells which produces the walls of the blood vessels is very slow, with cell renewal times which are measured in years.

Abnormal angiogenesis (that is to say, stimulation of the growth of new blood vessels owing to a pathological syndrome) is an established characteristic of many diseases, especially diabetic retinopathy, rheumatoid arthritis, haemangioma and the growth of solid tumours. Angiogenesis can also play an important part in other diseases, such as arterio-coronary disease.

In the field of oncology it has been shown that the growth of solid tumours is totally dependent upon the constant development of new blood vessels and that this is in correlation, for the metastases of certain cancers, with the increasing size of the primary tumour (J. Folkman, *New Engl. Med.*, 285 (1974), 1182–1185).

Pharmaceutical treatment (that is to say, by means of an angiogenesis inhibitor) can, therefore, stop the growth of primary tumours, prevent or reduce the formation of metastases, and prevent the appearance of secondary growths. Such angiogenesis inhibitors are also useful in the treatment of non-neoplasic diseases mentioned above in which angiogenic activity occurs.

The needs of therapeutics demand the constant development of new angiogenesis-inhibiting compounds with the aim of obtaining active ingredients that are more active, more specific and, at the same time, less toxic.

The present invention relates to new compounds that have a tetrahydropyran structure and that are structurally and pharmacologically original as compared with the compounds described in the prior art.

More particularly, the present invention relates to compounds of the general formula (I):

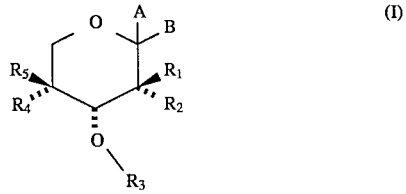

in which:

A - either represents —$OR_6$, and B represents —$CH_2$—X,
- or, together with B and the carbon atom carrying them, forms an oxygen-containing heterocycle selected from oxirane, 2,2-dimethyl[1,3]dioxolane and [1,3]dioxolan-2-one, $R_1$ - either represents the radical:

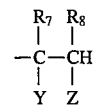

in which Y and Z either each represent hydrogen or together form a double bond or together form, with the carbon atoms carrying them, an oxirane ring, and $R_2$ is selected from hydrogen, a hydroxy radical and the radical —$OR_9$,

- or represents the radical:

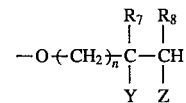

in which n is an integer from 1 to 4 inclusive and Y and Z either each represent hydrogen or together form a double bond or together form, with the carbon atoms carrying them, an oxirane ring, and $R_2$ represents hydrogen,

- or $R_1$ represents hydrogen
and $R_2$ represents the radical:

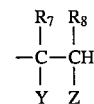

as defined above, $R_3$ is selected from hydrogen, a linear or branched, optionally substituted alkyl radical having from 1 to 6 carbon atoms, an optionally substituted benzyl radical, an optionally substituted benzoyl radical, an optionally substituted formyl radical, a linear or branched, optionally unsaturated and optionally substituted acyl radical having from 1 to 6 carbon atoms, an allyl radical, and an optionally mono- or di-substituted carbamoyl radical, $R_4$ - either is selected from a hydroxy radical, a linear or branched, optionally substituted alkoxy radical having from 1 to 6 carbon atoms, an optionally mono- or di-substituted carbamoyloxy radical, a piperazinylcarbonyloxy radical substituted in the 4-position by the radical $R_9$, and an imidazol-1-ylcarbonyloxy radical, and $R_5$ represents hydrogen,

- or, together with $R_5$ and the carbon atom carrying them, forms a carbonyl group, $R_6$, $R_7$ and $R_8$ are selected, each independently of the others, from hydrogen, a linear or branched, optionally substituted alkyl radical having from 1 to 6 carbon atoms, and a phenylalkyl radical in which the phenyl group is optionally substituted and the alkyl group, which is linear or branched and is optionally substituted, has from 1 to 6 carbon atoms, $R_9$ is selected from hydrogen, a linear or branched, optionally substituted alkyl radical having from 1 to 6 carbon atoms, an optionally substituted formyl radical, a linear or branched, optionally unsaturated and optionally substituted acyl radical having from 1 to 6 carbon atoms, a linear or branched, optionally substituted alkoxycarbonyl radical having from 1 to 6 carbon atoms, an optionally substituted benzyl radical, and an optionally mono- or di-substituted carbamoyl radical, X is selected from a hydroxy radical, a halogen atom, an optionally substituted phenylsulfonyloxy radical, and an optionally substituted linear or branched alkylsulfonyloxy radical having from 1 to 6 carbon atoms, where appropriate their optical and geometrical isomers, in pure form or in the form of a mixture, and, where appropriate, their pharmaceutically acceptable addition salts with an acid, wherein:
- the term "optionally mono- or di-substituted" associated with the above-defined carbamoyl and carbamoyloxy radicals indicates that one or both of the hydrogen atoms carried by the nitrogen atom may be substituted (independently of each other when both hydrogen atoms are substituted) by:
  - a linear or branched, optionally substituted alkyl radical having from 1 to 6 carbon atoms,
  - an optionally substituted formyl radical,
  - a linear or branched, optionally unsaturated and optionally substituted acyl radical having from 1 to 6 carbon atoms,
  - an optionally substituted benzoyl radical,
  - an optionally substituted phenyl radical,
  - an optionally substituted naphthyl radical, and
  - an amino radical optionally substituted by one or two alkyl radicals having from 1 to 6 carbon atoms in a straight or branched chain, each alkyl radical being optionally substituted,
- the term "optionally substituted" associated with the alkyl, alkoxy, alkoxycarbonyl, formyl, acyl, benzyl, benzoyl, phenyl and naphthyl radicals indicates that those radicals may be substituted by one or more chemical entities selected from hydroxy, halogen, trihalomethyl, amino, alkylamino, dialkylamino, linear or branched alkoxy having from 1 to 6 carbon atoms, linear or branched alkoxycarbonyl having from 1 to 6 carbon atoms, and linear or branched acyl having from 1 to 6 carbon atoms,
- the term "optionally substituted" associated with the alkylsulfonyloxy and phenylsulfonyloxy radicals indicates that those radicals may be substituted by one or more linear or branched alkyl radicals having from 1 to 6 carbon atoms, and
- the term "unsaturated acyl radical" is to be understood as meaning more especially the acryloyl and methacryloyl radicals.

In the present invention, carbamoyl radical is to be understood as meaning the radical

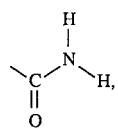

and carbamoyloxy radical is to be understood as meaning the radical

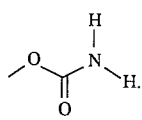

Of the acids that can be used for the formation of pharmaceutically acceptable salts there may be mentioned, by way of non-limiting example, hydrochloric acid, phosphoric acid, sulfuric acid, tartaric acid, citric acid, maleic acid, fumaric acid, etc..

The present invention relates also to a process for the preparation of a compound of formula (I), characterised in that 1,2:4,5-di-O-isopropylidene-β-D-fructopyranose of formula (II):

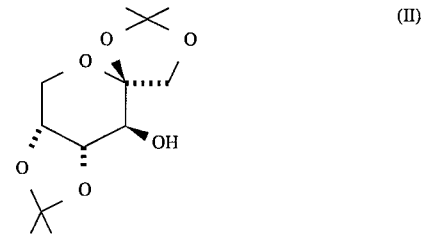

prepared in accordance with the procedure described by E. J. Prisbe et al. (*J. Org. Chem.*, 41, (1976), 1836–1846), is subjected either: to an oxidising agent, such as pyridinium dichromate, so as to obtain the ketone of formula (III):

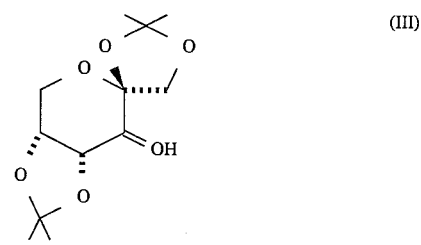

which is subjected to the action of a compound of formula (IVa) prepared from the corresponding vinyl halide:

in which $R_7$ and $R_8$ are selected, each independently of the other, from hydrogen, a linear or branched, optionally substituted alkyl radical having from 1 to 6 carbon atoms, and a phenylalkyl radical in which the phenyl group is optionally substituted and the alkyl group, which is linear or branched and is optionally substituted, has from 1 to 6 carbon atoms, in order to obtain the compound of formula ($Va_1$):

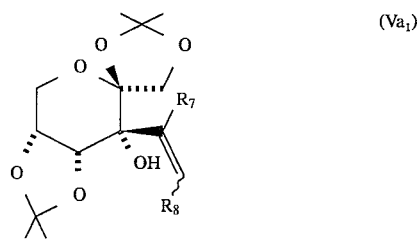

in which $R_7$ and $R_8$ are as defined above, which may optionally be subjected to the action of an alkyl halide, an acyl halide, a benzyl halide, an alkyl haloformate or an isocyanate in order to yield the compound of formula ($Va_2$):

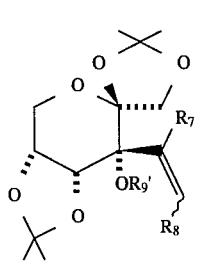

(Va₂)

in which R₇ and R₈ are as defined above and R'₉ is selected from a linear or branched, optionally substituted alkyl radical containing from 1 to 6 carbon atoms, an optionally substituted formyl radical, an optionally substituted acyl radical containing from 1 to 6 carbon atoms, an optionally substituted benzyl radical, a linear or branched, optionally substituted alkoxycarbonyl radical containing from 1 to 6 carbon atoms, and an optionally mono- or di-substituted carbamoyl radical, which compound of formula (Va₁) may optionally be subjected to the action of methyloxalyl chloride, in the presence of n-butyllithium, so as to obtain the compound of formula (Va₃):

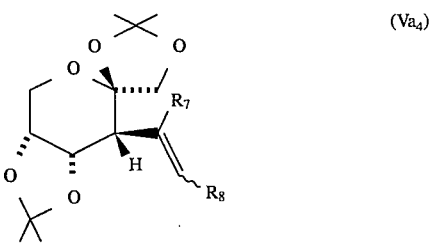

(Va₃)

in which R₇ and R₈ are as defined above, which is then subjected to the action of tributyltin hydride in order to yield the compound of formula (Va₄):

(Va₄)

in which R₇ and R₈ are as defined above, the totality of the compounds of formulae (Va₁) and (Va₂) forming the compound of formula (Va):

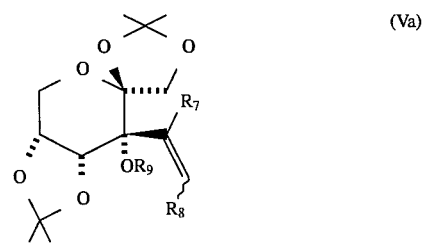

(Va)

in which R₇ and R₈ are as defined above and R₉ is selected from hydrogen and the radical R'₉ as defined above, or: directly to the action of a compound of formula (IVb):

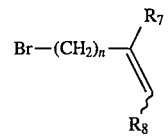

(IVb)

in which R₇ and R₈ are as defined above and n is an integer from 1 to 4 inclusive, in order to obtain the compound of formula (Vb):

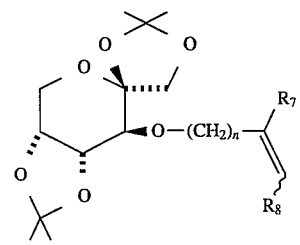

(Vb)

in which R₇, R₈ and n are as defined above, the compounds of formulae (Va₄), (Va) and (Vb) then being hydrolysed in an acidic medium, for example acetic acid, to yield the diols of formulae (VIa₄), (VIa) and (VIb), respectively:

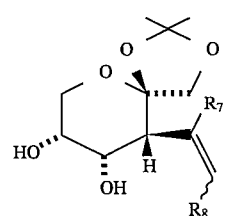

(VIa₄)

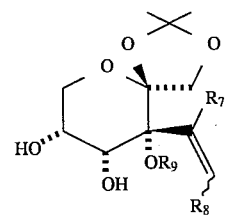

(VIa)

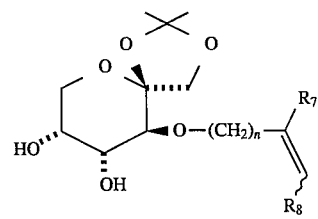

(VIb)

in which R₇, R₈, R₉ and n are as defined above, which compounds of formulae (VIa₄), (VIa) and (VIb) may be regioselectively substituted in the presence of dibutyltin oxide so as to obtain the compounds of formulae (VIIa₄), (VIIa) and (VIIb), respectively:

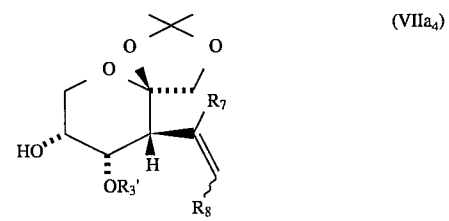

(VIIa₄)

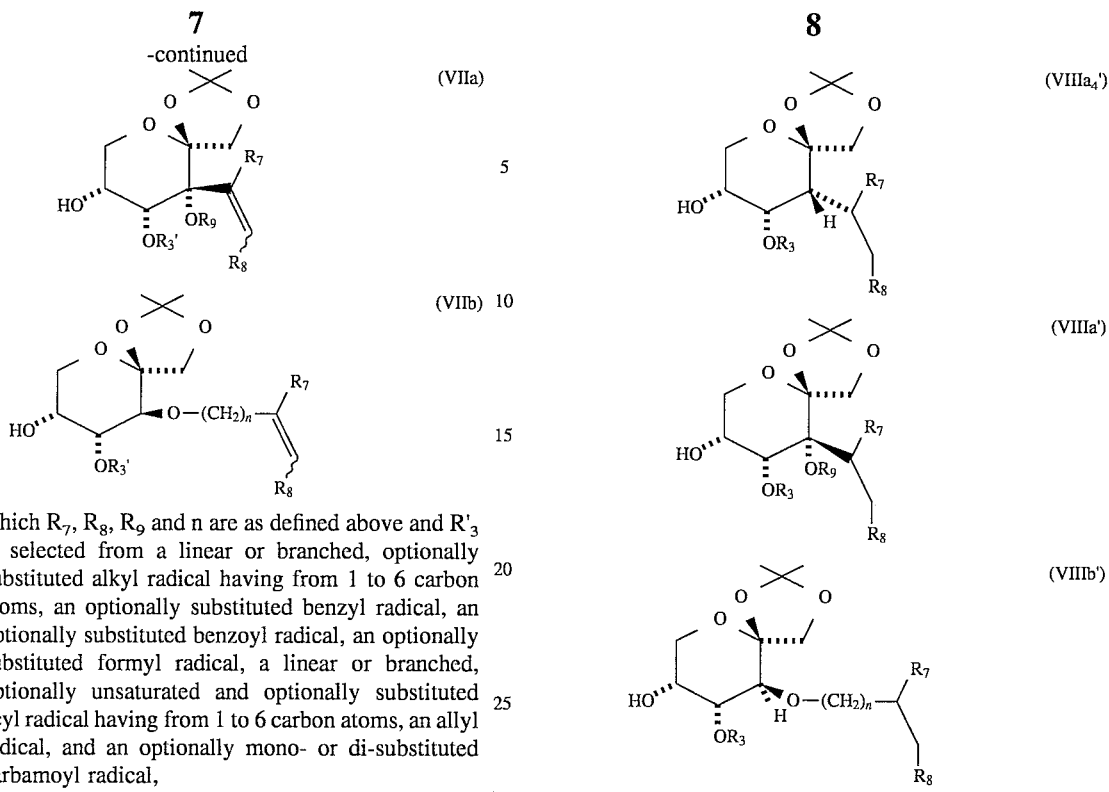

in which $R_7$, $R_8$, $R_9$ and n are as defined above and $R'_3$ is selected from a linear or branched, optionally substituted alkyl radical having from 1 to 6 carbon atoms, an optionally substituted benzyl radical, an optionally substituted benzoyl radical, an optionally substituted formyl radical, a linear or branched, optionally unsaturated and optionally substituted acyl radical having from 1 to 6 carbon atoms, an allyl radical, and an optionally mono- or di-substituted carbamoyl radical, it being possible for all of the compounds of formulae (VIa$_4$) and (VIIa$_4$), (VIa) and (VIIa) and (VIb) and (VIIb) optionally to be subjected to an epoxidation reagent, such as 3-chloroperbenzoic acid, in order to yield the compounds of formulae (VIIIa$_4$), (VIIIa) and (VIIIb), respectively:

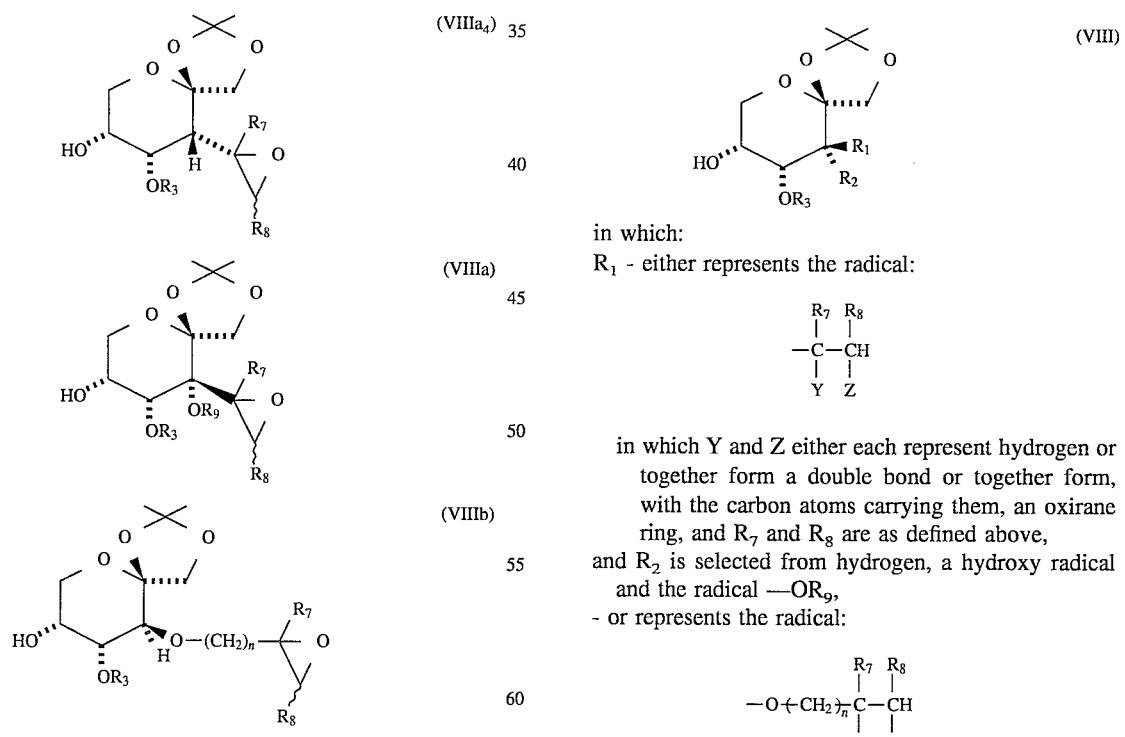

in which $R_7$, $R_8$, $R_9$ and n are as defined above and $R_3$ is selected from hydrogen and the radical $R'_3$ as defined above, or alternatively to be subjected to catalytic hydrogenation in order to obtain the compounds of formulae (VIII'a$_4$), (VIII'a) and (VIII'b), respectively:

in which $R_3$, $R_7$, $R_8$, $R_9$ and n are as defined above, the totality of the compounds of formulae (VIa$_4$), (VIa), (VIb), (VIIa$_4$), (VIIa), (VIIb), (VIIIa$_4$), (VIIIa), (VIIIb), (VIII'a$_4$), (VIII'a) and (VIII'b) forming the compound of formula (VIII):

in which:

$R_1$ - either represents the radical:

$$\begin{array}{c} R_7 \;\; R_8 \\ | \;\;\; | \\ -C-CH \\ | \;\;\; | \\ Y \;\;\; Z \end{array}$$

in which Y and Z either each represent hydrogen or together form a double bond or together form, with the carbon atoms carrying them, an oxirane ring, and $R_7$ and $R_8$ are as defined above, and $R_2$ is selected from hydrogen, a hydroxy radical and the radical —$OR_9$,

- or represents the radical:

$$-O(CH_2)_n \begin{array}{c} R_7 \;\; R_8 \\ | \;\;\; | \\ -C-CH \\ | \;\;\; | \\ Y \;\;\; Z \end{array}$$

in which n is an integer from 1 to 4 inclusive and $R_7$, $R_8$, Y and Z are as defined above, and $R_2$ represents hydrogen,

- or $R_1$ represents hydrogen and $R_2$ represents the radical:

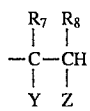

as defined above, and $R_3$ is as defined above, the compound of formula (VIII) then optionally being subjected:

- to the action of an alkylating agent under customary conditions, for example after formation of an anion by means of sodium hydride,
- to the action of an isocyanic compound in the presence or absence of an activator, such as 4-dimethylaminopyridine,
- or to the action of a carbonylating compound, carbonyldiimidazole, yielding the compound of formula (IXa):

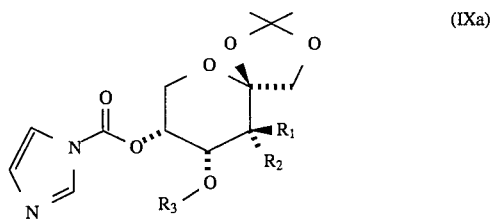

in which $R_1$, $R_2$ and $R_3$ are as defined above, which compound, under the action of a piperazine substituted in the 4-position by the radical $R_9$, itself yields the compound of formula (IXb):

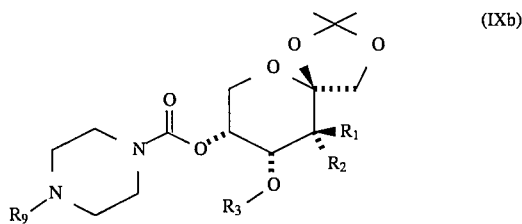

in which $R_1$, $R_2$, $R_3$ and $R_9$ are as defined above, the totality of the compounds of formulae (VIII), (IXa) and (IXb) forming the compound of formula (IX):

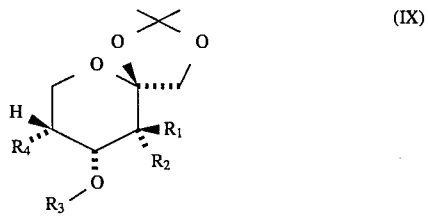

in which $R_1$, $R_2$ and $R_3$ are as defined above and $R_4$ is selected from a hydroxy radical, a linear or branched, optionally substituted alkoxy radical having from 1 to 6 carbon atoms, an optionally mono- or di-substituted carbamoyloxy radical, a piperazinylcarbonyloxy radical substituted in the 4-position by the radical $R_9$, and an imidazolylcarbonyloxy radical, it also being possible for the compound of formula (VIII) to be subjected to the action of an oxidising agent under the conditions employed for the preparation of the compound of formula (III), so as to obtain the compound of formula (X):

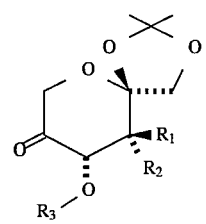

in which $R_1$, $R_2$ and $R_3$ are as defined above,
the totality of the compounds of formulae (IX) and (X) forming the compound of formula (XI):

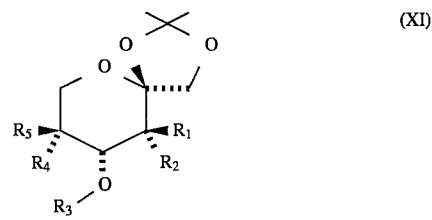

in which $R_1$, $R_2$ and $R_3$ are as defined above and $R_4$ and $R_5$ are as defined for formula (I), which compound (XI) may be:

- either: treated in accordance with customary methods of alcoholysis in order to form the compound of formula (XII):

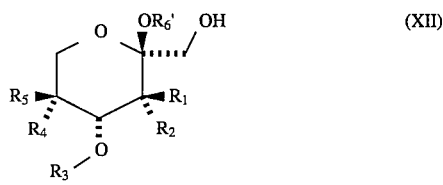

in which $R_1$, $R_2$, $R_3$, $R_4$ and $R_5$ are as defined above and $R'_6$ is selected from a linear or branched, optionally substituted alkyl radical having from 1 to 6 carbon atoms, and a phenylalkyl radical in which the phenyl group is optionally substituted and the alkyl group, which is linear or branched and is optionally substituted, has from 1 to 6 carbon atoms, then subjected to customary substitution reactions so as to obtain the compound of formula (XIII):

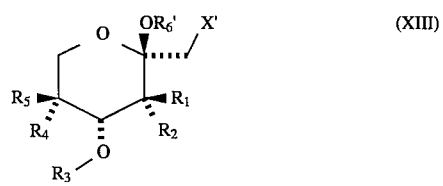

in which $R_1$, $R_2$, $R_3$, $R_4$, $R_5$ and $R'_6$ are as defined above and X' is selected from a halogen atom, an optionally substituted phenylsulfonyloxy radical, and an optionally substituted linear or branched alkylsulfonyloxy radical having from 1 to 6 carbon atoms,

- or: hydrolysed, under the action of an acidic resin, for example, to form the diol of formula (XIV):

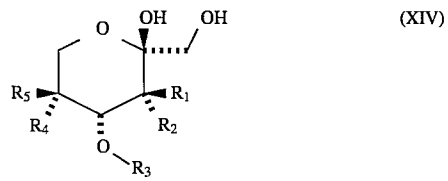

in which $R_1$, $R_2$, $R_3$, $R_4$ and $R_5$ are as defined above, then optionally subjected to customary substitution reactions so as to obtain the compound of formula (XV):

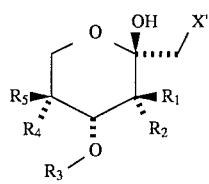

in which $R_1$, $R_2$, $R_3$, $R_4$, $R_5$ and X' are as defined above, which compound of formula (XV), when X' represents an iodine atom, can be converted, under the action of silver oxide, into the epoxide of formula (XVI):

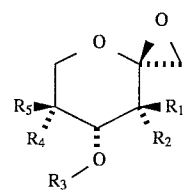

in which $R_1$, $R_2$, $R_3$, $R_4$ and $R_5$ are as defined above, it also being possible for the compound of formula (XIV) to be subjected to the action of N,N-carbonyldiimidazole to yield the compound of formula (XVII):

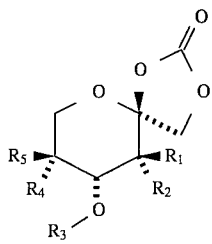

in which $R_1$, $R_2$, $R_3$, $R_4$ and $R_5$ are as defined above, the compounds of formulae (XI), (XII), (XIII), (XIV), (XV), (XVI) and (XVII) forming the compound of formula (I), which is optionally purified by a customary purification method and the optical and geometrical isomers of which are separated, if desired, by a customary separation method, and which are optionally converted into their pharmaceutically acceptable addition salts with an acid.

The compound of formula (Va$_1$) in which $R_7$ represents hydrogen can advantageously be obtained by reaction of an organolithium compound, prepared from the corresponding propargyl compound, of formula (IVa'):

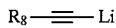

in which $R_8$ is as defined above,
then by catalytic hydrogenation of the resulting alkyne of formula (Va$_1$'):

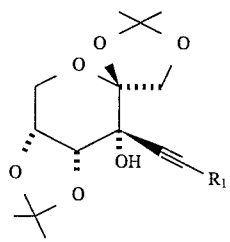

in which $R_8$ is as defined above.
The compound of formula (VIII) can be protected regioselectively in the form of a silylated compound of formula (VIII'):

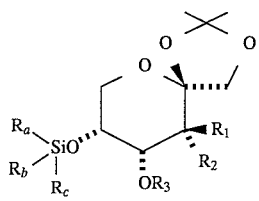

in which $R_1$ and $R_2$ are as defined above and $R_a$, $R_b$ and $R_c$ each independently of the others represent a linear or branched alkyl radical containing from 1 to 6 carbon atoms, or a phenyl radical.

In general, the protection and deprotection of the hydroxy radicals carried by the pyranose compounds, the catalytic hydrogenation reactions and the epoxidation reactions by means of 3-chloroperbenzoic acid can be carried out at the time considered appropriate by the person skilled in the art, in the course of the synthesis of each compound.

The compounds of formula (I) have valuable pharmacological properties. In fact, the compounds are powerful angiogenesis inhibitors which have the advantage of being much less toxic as compared with the reference compounds. They therefore have an excellent therapeutic index. Accordingly, the compounds can be used in therapeutics as anti-tumour agents, in the inhibition of the formation and growth of metastases, as well as in the treatment of diabetic retinopathy, rheumatoid arthritis, haemangioma and arterio-coronary diseases, and more generally in disorders due to or associated with angiogenesis disorders.

The present invention relates also to pharmaceutical compositions comprising the compounds of formula (I), their stereoisomers, where appropriate, or, where appropriate, their pharmaceutically acceptable addition salts with an acid, on their own or in combination with one or more inert, non-toxic excipients or carriers.

Of the pharmaceutical compositions according to the invention there may be mentioned more especially those which are suitable for oral, parenteral, nasal, rectal, perlingual, ocular or respiratory administration, especially tablets, dragées, sublingual tablets, sachets, paquets, gelatin capsules, glossettes, lozenges, suppositories, creams, ointments, dermic gels, injectable or drinkable preparations, aerosols, ocular or nasal drops.

The dosage used varies according to the age and weight of the patient, the mode of administration and the nature of the therapeutic indication and of any associated treatments, and ranges from 0.01 to 1 g per day, in one or more administrations.

The Examples which follow illustrate the invention but do not limit it in any way. The starting materials are known or are prepared by known procedures.

The nomenclature used for naming the compounds of the invention is that recommended in "Modern Carbohydrate Chemistry" by Roger W. Binkley, Editions Marcel Dekker Inc., New York (1988).

The numbering and stereochemistry of β-D-psicopyranose which are used in the Examples which follow comply with the formula:

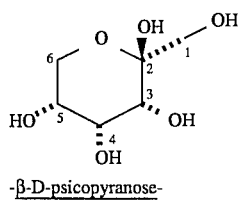

-β-D-psicopyranose-

The numbering and stereochemistry of β-D-fructopyranose which are used in the Examples which follow comply with the formula:

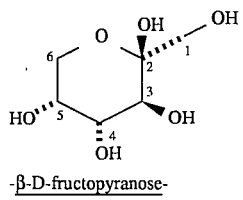

-β-D-fructopyranose-

Example 1:
1,2-O-Isopropylidene-3-isopropenyl-β-D-psicopyranose

Step A: 1,2:4,5-di-O-isopropylidene-β-n-erythro-2,3-hexodiulo-2,6-pyranose 2.44 g of 0.3 nm molecular sieve are added to 1.00 g (3.84 mmol) of 1,2:4,5-di-O-isopropylidene-β-D-fructopyranose, prepared in accordance with the procedure described by Prisbe E. J. et al. (*J. Org. Chem.*, 41, (1976), 1836), dissolved in 20 ml of anhydrous methylene chloride. The reaction mixture is cooled to 10° C. with the aid of an ice-bath, and 1.38 g (6.48 mmol) of pyridinium dichromate followed by 0.3 ml (5.24 mmol) of glacial acetic acid are added. The reaction mixture is stirred at 10° C. for 5 hours and is then concentrated (to 5 ml) in vacuo. 30 ml of diethyl ether are added and the whole is filtered. The filtrate is then evaporated and the resulting solid residue is chromatographed on silica gel (eluant: ethyl acetate/pentane, 3:2). 0.81 g (3.14 mmol) of the desired product in the form of a white-coloured solid is isolated.

Yield: 81%

Spectral characteristics:

$^1$H NMR (DMSO) δ(ppm): 1.30 (3H, s); 1.31 (3H, s); 1.35 (3H, s); 1.48 (3H, s); 3.90 (1H, d); 4.05 (1H, d); 4.25 (1H, d); 4.40 (1H, d); 4.61 (1H, dd); 4.82 (1H, d).

Step B: 1,2:4,5-di-O-isopropylidene-3-isopropenyl-β-D-psicopyranose 5.69 ml of tert.-butyllithium (1.7M in pentane, i.e. 9.67 mmol) are added dropwise, under a nitrogen atmosphere, to a solution, cooled to −78° C., of 1.03 ml of 2-bromopropene (1.40 g; 11.59 mmol) in 8.5 ml of anhydrous diethyl ether. The whole is stirred at −78° C. for 5 minutes and then at 0° C. for one hour. The solution is then added dropwise to a solution, cooled to −78° C., of the product obtained in step A (1 g; 3.87 mmol) in 15 ml of anhydrous toluene. After 45 minutes' stirring at −78° C., the reaction mixture is poured into a 10% aqueous ammonium chloride solution (40 ml) cooled to 0° C. The whole is diluted with diethyl ether (100 ml) and the reaction mixture is extracted. Customary treatment of the organic phase yields an oily residue, which is chromatographed on silica gel (eluant: pentane/ethyl acetate, 8:1). 0.55 g (1.83 mmol) of the desired product is obtained in the form of a white foam.

Yield: 47%

Spectral characteristics:

$^1$H NMR (DMSO) δ(ppm): from 1.25 to 1.50 (12H, m); 1.85 (3H, s); 3.40 (1H, s, exchangeable with D$_2$O); 3.80 (1H, d); 4.00 (1H, d); 4.05 (2H, d); 4.34 (1H, dd); 4.45 (1H, d); 5.10 (1H, s); 5.25 (1H, s).

Step C: 1,2-O-isopropylidene-3-isopropenyl-β-D-psicopyranose

A solution of 4 g (13.32 mmol) of the compound obtained in step B in 100 ml of an acetic acid/water mixture, 4:1, is stirred at room temperature for 17 hours. The solvents are evaporated off under reduced pressure, the residue is taken up in 50 ml of toluene, and then evaporation is carried out again. That operation is repeated twice to yield, after 24 hours' drying under a high vacuum, 3.28 g (12.60 mmol) of the desired compound (purity >99% by gas chromatography) in the form of a white-coloured powder.

Yield: 96%

Spectral characteristics:

$^1$H NMR (DMSO) δ(ppm): 1.30 (3H, s); 1.38 (3H, s); 1.85 (3H, s); 3.65 (1H, d); 3.75 (1H, d); 3.81 (1H, m); 3.82 (1H, m); 3.85 (1H, d); 4.10 (1H, d); 4.55 (1H, d, exchangeable with D$_2$O); 5.05 (1H, s); 5.08 (1H, s, exchangeable with D$_2$O); 5.16 (1H, s); 5.60 (1H, d, exchangeable with D$_2$O).

Example 2:
1,2-O-Isopropylidene-3-isopropenyl-4-O-methyl-β-D-psicopyranose 7.65 g (30.70 mmol) of dibutyltin oxide are added to a solution of 4 g (15.37 mmol) of the compound obtained in Example 1 in 120 ml of methanol. The heterogeneous reaction mixture is stirred and heated at reflux until a clear solution is obtained (approximately 24 hours). The mixture is cooled and then the solvent is evaporated off under reduced pressure. The solid residue is taken up in 70 ml of dioxane and is stirred under a nitrogen atmosphere. 6 ml (96.37 mmol) of methyl iodide are added and the whole is heated at reflux until the starting material has disappeared completely (approximately 60 hours). The dioxane is then evaporated off in vacuo and the resulting solid residue is chromatographed on silica gel (eluant: pentane/ethyl acetate, 2:1 then 1:1). 3.8 g (13.85 mmol) of the desired compound in the form of a white solid are obtained.

Yield: 90%

Spectral characteristics:

$^1$H NMR (DMSO) δ(ppm): 1.25 (3H, s); 1.32 (3H, s); 1.80 (3H, s); 3.28 (3H, s); 3.50 (1H, d); 3.70 (2H, d); 3.82 (1H, d); 4.08 (1H, d); 4.18 (1H, s broad); 5.02 (1H, s); 5.15 (1H, s); 5.38 (1H, s, exchangeable with D$_2$O); 5.70 (1H, s broad, exchangeable with D$_2$O).

Example 3:
5-O-Chloroacetylcarbamoyl-1,2-O-isopropylidene-3-isopropenyl-4-O-methyl-β-D-psicopyranose 2.39 ml (3.35 g; 28.05 mmol) of chloroacetyl isocyanate are added dropwise, under a nitrogen atmosphere, to a solution, cooled to 0° C., of 5.00 g (18.23 mmol) of the compound obtained in Example 2 in 90 ml of anhydrous methylene chloride. After 40 minutes' stirring at 0° C., the reaction mixture is poured into 50 ml of ice-water and the whole is stirred for one hour. After customary treatment of the organic phase and purification of the crude product by chromatography on silica gel (eluant: diethyl ether/petroleum ether, 4:1), 5.7 g (14.47 mmol) of the desired compound in the form of a white-coloured foam are obtained.

Yield: 79%

Spectral characteristics:

$^1$H NMR (DMSO) δ(ppm): 1.30 (3H, s); 1.40 (3H, s); 1.83 (3H, s); 3.29 (3H, s); 3.75 to 3.90 (3H, m); 4.00 (1H, d); 4.10 (1H, s, exchangeable with D$_2$O); 4.12 (1H, d); 4.46 (2H, s); 5.09 (1H, s broad); 5.29 (1H, d); 5.41 (1H, s); 11.02 (1H, s, exchangeable with D$_2$O).

Elemental analysis: (empirical formula: C$_{16}$H$_{24}$ClNO$_8$ M=393.82)

|        | C     | H    | N    | Cl   |
|--------|-------|------|------|------|
| % found | 48.78 | 5.80 | 3.82 | 9.03 |
| % calc. | 48.80 | 6.14 | 3.56 | 9.00 |

Example 4:
5-O-Chloroacetylcarbamoyl-1,2-O-isopropylidene-3-(2-methyloxiran-2-yl)-4-O-methyl-β-D-psicopyranose 5.00 g (21.15 mmol) of 72% 3-chloroperbenzoic acid are added to a solution of 5.70 g (14.47 mmol) of the compound obtained in Example 3 in 140 ml of methylene chloride. The reaction mixture is stirred at room temperature for 15 hours. The solid formed during the reaction is filtered and then the filtrate is evaporated under reduced pressure. The solid residue is purified by chromatography on silica gel (eluant: ethyl acetate/pentane, 2:1). The desired compound (4.20 g; 10.25 mmol) is obtained in the form of a white-coloured solid.

Yield: 70%

Spectral characteristics:

$^1$H NMR (DMSO) δ(ppm): 1.40 (6H, s); 1.40 (3H, s); 2.45 (1H, d); 2.80 (1H, d); 3.33 (3H, s); 3.75 to 3.81 (3H, m); 3.85 (1H, s, exchangeable with D$_2$O); 4.00 (1H, d); 4.22 (1H, d); 4.46 (2H, s); 5.35 (1H, s broad); 10.90 (1H, s, exchangeable with D$_2$O).

Elemental analysis: (empirical formula: C$_{16}$H$_{24}$ClNO$_9$ M=409.82)

|        | C     | H    | N    | Cl   |
|--------|-------|------|------|------|
| % found | 46.89 | 5.78 | 3.29 | 8.64 |
| % calc. | 46.89 | 5.90 | 3.42 | 8.65 |

Example 5:
1,2-O-Isopropylidene-3-isopropenyl-4-O-methyl-5-O-methylcarbamoyl-β-D-psicopyranose 0.90 ml (0.83 g; 14.56 mmol) of methyl isocyanate is added dropwise, under a nitrogen atmosphere, to a solution, cooled to 0° C. and containing 1.34 g (10.97 mmol) of 4-dimethylaminopyridine, of 2.00 g (7.29 mmol) of the compound obtained in Example 2 in 40 ml of anhydrous methylene chloride. After one hour's stirring at 0° C., the reaction mixture is poured into 20 ml of ice-water and the whole is stirred for one hour. After customary treatment of the organic phase and then purification of the crude product by chromatography on silica gel (eluant: diethyl ether), 2.3 g (6.94 mmol) of the desired compound in the form of a white-coloured foam are obtained.

Yield: 95%

Spectral characteristics:

$^1$H NMR (DMSO) δ(ppm): 1.30 (3H, s); 1.40 (3H, s); 1.80 (3H, s); 2.60 (3H, d); 3.25 (3H, s); 3.70 to 3.75 (3H, t); 3.89 (1H, s, exchangeable with D$_2$O); 3.90 (1H, d); 4.12 (1H, d); 5.02 (1H, s); 5.20 (1H, s); 5.25 (1H, s); 7.30 (1H, q, exchangeable with D$_2$O).

Example 6:
1,2-O-Isopropylidene-3-(2-methyloxiran-2-yl)-4-O-methyl-5-O-methylcarbamoyl-β-D-psicopyranose This compound is obtained in a manner identical to that described in Example 4, starting from 0.20 g (0.60 mmol) of the compound obtained in the preceding Example, 0.15 g (1.78 mmol) of solid sodium hydrogen carbonate and 0.22 g (0.93 mmol) of 72% 3-chloroperbenzoic acid.

Yield: 72%

Spectral characteristics:

$^1$H NMR (DMSO) δ(ppm): 1.35 (9H, s); 2.40 (1H, d); 2.60 (3H, s); 2.75 (1H, d); 3.30 (3H, s); 3.65 (1H, s, exchangeable with D$_2$O); 3.70 to 3.80 (3H, m); 3.90 (1H, d); 4.20 (1H, d); 5.20 (1H, s broad); 7.20 (1H, q, exchangeable with D$_2$O).

Elemental analysis: (empirical formula: C$_{15}$H$_{25}$NO$_8$ M=347.37)

|        | C     | H    | N    |
|--------|-------|------|------|
| % found | 51.95 | 7.25 | 4.09 |
| % calc. | 51.87 | 7.25 | 4.03 |

Example 7:
5-O-Benzoylcarbamoyl-1,2-O-isopropylidene-3-isopropenyl-4-O-methyl-β-D-psicopyranose Following the procedure described for the preparation of Example 5, starting from 1.20 g (4.37 mmol) of the compound obtained in Example 2 and 0.96 g (6.52 mmol) of benzoyl isocyanate, and after purification by chromatography on silica gel (eluant: diethyl ether/methylene chloride, 2:1), 1.30 g (3.08 mmol) of the desired product are obtained.

Yield: 70%

Spectral characteristics:

$^1$H NMR (DMSO) δ(ppm): 1.30 (3H, s); 1.40 (3H, s); 1.85 (3H, s); 3.31 (3H, s); 3.72 (1H, d); 3.80 (1H, d); 3.89 (1H, d); 4.05 (1H, d); 4.15 (1H, d); 4.40 (1H, s, exchangeable with D$_2$O); 5.05 (1H, s broad); 5.25 (1H, s broad); 5.50 (1H, s broad); 7.52 (2H, t); 7.62 (1H, t); 7.90 (2H, d); 11.12 (1H, s, exchangeable with D$_2$O).

Example 8:
5-O-Benzoylcarbamoyl-1,2-O-isopropylidene-3-(2-methyloxiran-2-yl)-4-O-methyl-β-D-psicopyranose Following the procedure described for the preparation of Example 4, starting from 0.25 g (0.59 mmol) of the compound obtained in Example 7 and 0.22 g (0.93 mmol) of 72% 3-chloroperbenzoic acid, then purification by chromatography on silica gel (eluant: diethyl ether/heptane, 5:1), 0.10 g (0.23 mmol) of the desired compound in the form of a white-coloured foam is collected.

Yield: 39%

Spectral characteristics:

¹H NMR (DMSO) δ(ppm): 1.40 (9H, s); 2.41 (1H, d); 2.81 (1H, d); 3.35 (3H, s); 3.70 to 3.82 (3H, m); 4.00 (1H, d); 4.25 (1H, d); 4.30 (1H, s, exchangeable with D₂O); 5.40 (1H, s broad); 7.52 (2H, t); 7.61 (1H, t); 7.88 (2H, d); 10.96 (1H, s, exchangeable with D₂O).

Elemental analysis: (empirical formula: $C_{21}H_{27}NO_9$ M=437.45)

|          | C     | H    | N    |
|----------|-------|------|------|
| % found  | 57.84 | 6.27 | 3.04 |
| % calc.  | 57.66 | 6.22 | 3.20 |

Example 9:
3-Isopropenyl-4-O-methyl-5-O-methylcarbamoyl-β-D-psicopyranose 20 g of acidic resin (DOWEX 50X8-100) are added to a suspension of 1.10 g (3.24 mmol) of the compound obtained in Example 5 in 40 ml of water. The whole is heated at 60° C. for 80 minutes and is then stirred at room temperature for 1.5 hours. The reaction mixture is filtered and the filtrate is evaporated to give 0.92 g (3.15 mmol) of the desired triol in the form of a white foam.

Yield: 97%

Spectral characteristics:

¹H NMR (DMSO) δ(ppm): 1.80 (3H, s); 2.60 (3H, d); 3.20 (3H, s); 3.35 to 3.60 (4H, m, of which 1H exchangeable with D₂O); 3.80 (1H, d); 4.00 (1H, m); 4.60 (1H, m, exchangeable with D₂O); 4.89 (1H, s broad); 5.15 (1H, s broad); 5.22 (1H, s broad); 5.50 (1H, s, exchangeable with D₂O); 7.25 (1H, q, exchangeable with D₂O).

Example 10:
1-(para-Toluenesulfonyl)-3-isopropenyl-4-O-methyl-5-O-methylcarbamoyl-β-D-psicopyranose 8.94 g (46.89 mmol) of tosyl chloride are added, at room temperature and under a nitrogen atmosphere, to a solution of 3.90 g (13.39 mmol) of the triol obtained in Example 9 in 40 ml of anhydrous pyridine. After 2 hours' stirring at room temperature, the reaction mixture is poured into 30 ml of an aqueous ammonium chloride solution (10%) cooled to 0° C. The reaction mixture is then diluted in 200 ml of ethyl acetate and then the two phases are separated. After customary treatment of the organic phase and purification of the crude product by chromatography on silica gel (eluant: diethyl ether), 4.98 g (11.18 mmol) of the desired product in the form of a white foam are obtained.

Yield: 83%

Spectral characteristics:

¹H NMR (DMSO) δ(ppm): 1.70 (3H, s); 2.40 (3H, s); 2.70 (3H, d); 3.25 (3H, s); 3.60 (1H, d); 3.75 (1H, s, exchangeable with D₂O); 3.80 (1H, d); 3.90 to 4.00 (3H, m); 4.85 (1H, s broad); 5.05 (1H, s broad); 5.20 (1H, s broad); 6.60 (1H, s, exchangeable with D₂O); 7.22 (1H, q, exchangeable with D₂O); 7.48 (2H, d); 7.75 (2H, d).

Example 11:
1-(para-Toluenesulfonyl)-3-(2-methyloxiran-2-yl)-4-O-methyl-5-O-methylcarbamoyl-β-D-psicopyranose Following the procedure described for the preparation of Example 4, starting from 0.25 g (0.56 mmol) of the compound obtained in the preceding Example and 0.21 g (0.89 mmol) of 72% 3-chloroperbenzoic acid, then purification by chromatography on silica gel (eluant: pentane/ethyl acetate, 1:1), 0.16 g of the desired product in the form of a white-coloured foam is obtained.

Yield: 61%

Spectral characteristics:

¹H NMR (DMSO) δ(ppm): 1.80 (3H, s); 2.20 (1H, d); 2.40 (3H, s); 2.50 (1H, m); 2.55 (3H, d); 3.25 (3H, s); 3.44 (1H, s, exchangeable with D₂O); 3.60 (1H, d); 3.80 to 3.85 (2H, m); 4.00 (1H, d); 4.10 (1H, d); 5.11 (1H, s broad); 6.72 (1H, s, exchangeable with D₂O); 7.05 (1H, q, exchangeable with D₂O); 7.49 (2H, d); 7.80 (2H, d).

Elemental analysis: (empirical formula: $C_{19}H_{27}NO_{10}S$ M=461.48)

|         | C     | H    | N    | S    |
|---------|-------|------|------|------|
| % found | 49.83 | 6.34 | 3.15 | 6.64 |
| % calc. | 49.45 | 5.90 | 3.04 | 6.95 |

Example 12: 1-Bromo-1-desoxy-3-isopropenyl-4-O-methyl-5-O-methylcarbamoyl-β-D-psicopyranose 0.29 g (3.34 mmol) of lithium bromide is added at room temperature, in a single portion, to a solution of 0.31 g (0.69 mmol) of the compound obtained in Example 10 in 15 ml of acetone. The reaction mixture is placed under stirring and then heated at 75° C. for 1.5 hours. A further 0.26 g (2.99 mmol) of lithium bromide is then added and the whole is again heated at 75° C. for one hour. The acetone is evaporated off under reduced pressure and the residue is taken up in 20 ml of ethyl acetate. Customary treatment of the organic phase yields 0.23 g (0.65 mmol) of the desired product in the form of a white-coloured foam.

Yield: 94%

Spectral characteristics:

¹H NMR (DMSO) δ(ppm): 1.80 (3H, s); 2.60 (3H, d); 3.22 (3H, s); 3.52 (1H, d); 3.70 (1H, d); 3.78 (1H, d); 3.82 (1H, s, exchangeable with D₂O); 3.89 (1H, d); 4.05 (1H, d); 4.95 (1H, s broad); 5.20 (1H, s broad); 5.23 (1H, s broad); 6.20 (1H, s, exchangeable with D₂O); 7.30 (1H, q, exchangeable with D₂O).

Example 13:
1-Bromo-1-desoxy-3-(2-methyloxiran-2-yl)-4-O-methyl-5-O-methylcarbamoyl-β-D-psicopyranose Following the procedure described for the preparation of Example 4, starting from 0.23 g (0.65 mmol) of the compound obtained in the preceding Example and 0.23 g (0.97 mmol) of 72% 3-chloroperbenzoic acid, then purification by chromatography on silica gel (eluant: diethyl ether), 0.16 g (0.43 mmol) of the desired compound in the form of a white-coloured solid is obtained.

Yield: 66%

Spectral characteristics:

¹H NMR (DMSO) δ(ppm): 1.35 (3H, s); 2.32 (1H, d); 2.58 (3H, d); 2.72 (1H, d); 3.28 (3H, s); 3.45 (1H, s, exchangeable with D₂O); 3.62 (1H, d); 3.69 (2H, s); 3.90 (1H, d); 3.99 (1H, d); 5.12 (1H, s broad); 6.32 (1H, s, exchangeable with D₂O); 7.10 (1H, q, exchangeable with D₂O).

Elemental analysis: (empirical formula: $C_{12}H_{20}BrNO_7$ M=370.20)

|         | C     | H    | N    | Br    |
|---------|-------|------|------|-------|
| % found | 38.72 | 5.18 | 3.83 | 21.64 |
| % calc. | 38.93 | 5.45 | 3.78 | 21.58 |

Example 14:
1,2-O-Isopropylidene-3-isopropenyl-4,5-di-O-methyl-β-D-psicopyranose 3.28 g (12.60 mmol) of the compound obtained in Example 1 in solution in 35 ml of anhydrous N,N-dimethylformamide are added dropwise, at room temperature, to a suspension of sodium hydride (60% in oil; 1.10 g; 27.50 mmol) in 50 ml of anhydrous N,N-dimethylformamide. The reaction mixture is stirred at room temperature for 30 minutes and is then cooled to 0° C. before the dropwise addition of 2.35 ml (5.36 g; 37.75 mmol) of methyl iodide. After 50 minutes' stirring at 0° C., the reaction mixture is poured into 100 ml of an aqueous ammonium chloride solution (10%) cooled to 0° C. Customary treatment of the organic phase yields, after purification by chromatography on silica gel (eluant: pentane/ethyl acetate, 8:1 then 5:1), 2.93 g (10.16 mmol) of the desired product in the form of a yellow-coloured oil.

Yield: 80%

Spectral characteristics:

$^1$H NMR (DMSO) δ(ppm): 1.29 (3H, s); 1.35 (3H, s); 1.80 (3H, s); 3.30 (3H, s); 3.40 (3H, s); 3.65 (1H, d); 3.72 (2H, m); 3.95 (1H, s); 3.97 (1H, d); 4.05 (1H, d); 4.49 (1H, s, exchangeable with $D_2O$); 5.02 (1H, s broad); 5.15 (1H, s broad).

Example 15:
1,2-O-Isopropylidene-3-(2-methyloxiran-2-yl)-4,5-di-O-methyl-β-D-psicopyranose Following the procedure described for the preparation of Example 4, starting from 0.44 g (1.52 mmol) of the compound obtained in Example 14 and 0.40 g (1.69 mmol) of 72% 3-chloroperbenzoic acid, then purification by chromatography on silica gel (eluant: pentane/ethyl acetate, 1.5:1), 0.27 g (0.89 mmol) of the desired compound in the form of a white-coloured solid is obtained.

Yield: 58%

Spectral characteristics:

$^1$H NMR (DMSO) δ(ppm): 1.40 (3H, s); 1.44 (6H, s); 2.22 (1H, d); 2.95 (1H, d); 3.35 (3H, s); 3.40 (3H, s); 3.60 (1H, d); 3.66 to 3.72 (2H, m); 3.92 (1H, d); 3.96 (1H, d); 4.40 (1H, s, exchangeable with $D_2O$); 4.56 (1H, d).

Elemental analysis: (empirical formula: $C_{14}H_{24}O_7$ M=304.34)

|         | C     | H    |
|---------|-------|------|
| % found | 55.92 | 7.99 |
| % calc. | 55.25 | 7.95 |

Example 16:
1,2-O-Isopropylidene-3-(2-methyloxiran-2-yl)-4-O-methyl-β-D-psicopyranose Following the procedure described for the preparation of Example 4, starting from 0.25 g (0.91 mmol) of the compound obtained in Example 2 and 0.34 g (1.44 mmol) of 72% 3-chloroperbenzoic acid, then purification by chromatography on silica gel (eluant: pentane/ethyl acetate, 2:1), 0.17 g (0.58 mmol) of the desired compound in the form of a white-coloured foam is obtained.

Yield: 63%

Spectral characteristics:

$^1$H NMR (DMSO) δ(ppm): 1.35 (9H, s); 2.42 (1H, d); 2.75 (1H, d); 3.20 (3H, s); 3.50 (1H, s); 3.65 to 3.85 (3H, m); 4.10 (1H, s broad); 4.20 (1H, d); 4.95 (1H, s, exchangeable with $D_2O$); 5.15 (1H, d, exchangeable with $D_2O$).

Elemental analysis: (empirical formula: $C_{13}H_{22}O_7$ M=290.31)

|         | C     | H    |
|---------|-------|------|
| % found | 54.14 | 7.73 |
| % calc. | 53.78 | 7.64 |

Example 17:
1,2-O-Isopropylidene-2,5-hexodiulo-3-(2-methyloxiran-2-yl)-4-O-methyl-β-D-erythro-2,6-pyranose 0.70 g (1.86 mmol) of pyridinium dichromate is added to a solution of the compound obtained in Example 16 (0.22 g; 0.76 mmol) in 5 ml of anhydrous methylene chloride containing 0.50 g of activated molecular sieve (0.4 nm). The whole is stirred at room temperature for 22 hours and then the reaction mixture is immediately chromatographed on silica gel (eluant: ethyl acetate/pentane, 2:1) to give 0.13 g (0.45 mmol) of the desired ketone in the form of a white-coloured solid.

Yield: 59%

Spectral characteristics:

$^1$H NMR (DMSO) δ(ppm): 1.45 (9H, s); 2.50 (1H, m); 2.80 (1H, d); 3.50 (3H, s); 3.85 (1H, d); 3.90 (1H, d); 4.20 (1H, d); 4.30 (1H, d); 4.50 (1H, s); 4.70 (1H, s, exchangeable with $D_2O$).

Elemental analysis: (empirical formula: $C_{13}H_{20}O_7$ M=288.30)

|         | C     | H    |
|---------|-------|------|
| % found | 53.77 | 7.05 |
| % calc. | 54.16 | 6.99 |

Example 18:
5-O-(1-Imidazolylcarbonyl)-1,2-O-isopropylidene-3-(2-methyloxiran-2-yl)-4-O-methyl-β-D-psicopyranose 3.35 g (20.66 mmol) of carbonyldiimidazole are added in a single portion, under a nitrogen atmosphere and at room temperature, to a solution of the compound obtained in Example 16 (2.00 g; 6.89 mmol) in 40 ml of anhydrous methylene chloride. The reaction mixture is stirred at room temperature for 5 hours. The solvent is then evaporated off under reduced pressure and the resulting solid residue is chromatographed on silica gel (eluant: ethyl acetate/pentane, 2:1). In this manner, 2.33 g (6.06 mmol) of the desired compound in the form of a white foam are obtained.

Yield: 88%

Spectral characteristics:

¹H NMR (DMSO) δ(ppm): 1.40 (9H, 2s); 2.80 (1H, m); 2.84 (1H, d); 3.40 (3H, s); 3.82 (1H, d); 3.90 (1H, d); 4.02 (2H, m); 4.25 (1H, d); 4.45 (1H, s, exchangeable with $D_2O$); 5.50 (1H, s broad); 7.06 (1H, s); 7.65 (1H, s); 8.30 (1H, s).

Elemental analysis: (empirical formula: $C_{17}H_{24}N_2O_8$ M=384.39)

|  | C | H | N |
|---|---|---|---|
| % found | 53.04 | 6.30 | 7.05 |
| % calc. | 53.12 | 6.29 | 7.29 |

Example 19:
5-O-{1-[4-((2,3,4-Trimethoxybenzyl)piperazinyl)]carbonyl}-1,2-O-isopropylidene-3-(2-methyloxiran-2-yl)-4-O-methyl-β-D-psicopyranose 1.50 g (5.63 mmol) of 4-[(2,3,4-trimethoxybenzyl)piperazine] (TRIMETAZIDINE®) are added, at room temperature and under a nitrogen atmosphere, to a solution of the compound obtained in Example 18 (1.00 g; 2.60 mmol) in 6 ml of anhydrous methylene chloride. The reaction mixture is stirred at room temperature for 17 hours and then the solvent is evaporated off under reduced pressure. The yellow-coloured oily residue that is obtained is purified on a column of silica gel (eluant: ethyl acetate). 1.15 g (1.97 mmol) of the desired product in the form of a white foam are isolated.

Yield: 75%

Spectral characteristics:

¹H NMR (DMSO) δ(ppm): 1.40 (9H, 2s); 2.25 (4H, s broad); 2.43 (1H, m); 2.80 (1H, d); 3.35 (6H, m); 3.60 (1H, s, exchangeable with $D_2O$); 3.70 (1H, m); 3.71 (3H, s); 3.75 (2H, m); 3.78 (9H, s); 3.90 (1H, d); 4.19 (1H, d); 5.15 (1H, d); 6.77 (1H, d); 6.96 (1H, d).

Elemental analysis: (empirical formula: $C_{28}H_{42}N_2O_{11}$ M=582.65)

|  | C | H | N |
|---|---|---|---|
| % found | 57.69 | 7.16 | 4.72 |
| % calc. | 57.72 | 7.27 | 4.81 |

Example 20:
5-O-[1-(4-Chloroacetylpiperazinyl)carbonyl]-1,2-O-isopropylidene-3-(2-methyloxiran-2-yl)-4-O-methyl-β-D-psicopyranose 1.5 g (2.74 mmol) of ceric ammonium nitrate are added at 0° C. to a solution of the compound obtained in Example 19 (0.50 g; 0.86 mmol) in 12 ml of an acetonitrile/water mixture (2:1). The reaction mixture is stirred for 2.5 hours, the temperature being allowed gradually to approach room temperature. After evaporation of the solvents, the residue is chromatographed on silica gel (eluant: methylene chloride/methanol/ammonia, 90: 10:0.5). 0.16 g (0.40 mmol) of debenzylated compound is obtained. To a solution of 0.15 g (0.37 mmol) of that compound in 5 ml of anhydrous methylene chloride containing 0.15 ml (0.11 g; 1.08 mmol) of anhydrous triethylamine there is added dropwise at 0° C., under a nitrogen atmosphere, 0.045 ml (0.064 g; 0.56 mmol) of chloroacetic acid chloride. The reaction mixture is stirred at 0° C. for 1 hour 45 minutes and then the whole is poured into an aqueous ammonium chloride solution (10%) cooled to 0° C. After customary treatment of the organic phase and then purification by chromatography on silica gel (eluant: ethyl acetate), 0.086 g (0.18 mmol) of the desired product in the form of a beige foam is obtained.

Overall yield: 22%

Spectral characteristics:

¹H NMR (DMSO) δ(ppm): 1.40 (9H, 3s); 2.43 (1H, d); 2.80 (1H, d); 3.30 (3H, s); 3.40 (8H, s broad); 3.80 (4H, m, of which 1 exchangeable with $D_2O$); 3.92 (1H, d); 4.20 (1H, d); 4.40 (2H, s); 5.18 (1H, s broad).

Elemental analysis: (empirical formula: $C_{20}H_{31}ClN_2O_9$ M=478.93)

|  | C | H | N | Cl |
|---|---|---|---|---|
| % found | 49.80 | 6.41 | 5.71 | 7.73 |
| % calc. | 50.16 | 6.52 | 5.85 | 7.40 |

Example 21:
5-O-[1-(4-Formylpiperazinyl)carbonyl]-1,2-O-isopropylidene-3-(2-methyloxiran-2-yl)-4-O-methyl-β-D-psicopyranose This synthesis is carried out under the same operating conditions as those described for the preparation of Example 19, starting from 0.50 g of the compound obtained in Example 18 (1.30 mmol) and 0.40 ml (0.44 g; 3.88 mmol) of N-formylpiperazine in 5 ml of anhydrous methylene chloride. 0.36 g (0.84 mmol) of the desired product in the form of a white-coloured powder is obtained.

Yield: 64%

Spectral characteristics:

¹H NMR (DMSO) δ(ppm): 1.40 (9H, s); 2.48 (1H, d); 2.80 (1H, d); 3.30 (3H, s); 3.35 (8H, m); 3.70 to 3.85 (4H, m, of which 1H exchangeable with $D_2O$); 3.92 (1H, d); 4.21 (1H, d); 5.20 (1H, s broad); 8.06 (1H, s).

Elemental analysis: (empirical formula: $C_{19}H_{30}N_2O_9$ M=430.46)

|  | C | H | N |
|---|---|---|---|
| % found | 52.95 | 6.99 | 6.51 |
| % calc. | 53.02 | 7.02 | 6.51 |

Example 22: 4,5-di-O-Chloroacetylcarbamoyl-1,2-O-isopropylidene-3-isopropenyl-β-D-psicopyranose Following the procedure described for the preparation of Example 3, starting from 0.50 g (1.82 mmol) of the compound obtained in Example 1 and 0.50 ml (0.70 g; 5.87 mmol) of chloroacetyl isocyanate, then purification by chromatography on silica gel (eluant: ethyl acetate/pentane, 1:1), 0.90 g (1.80 mmol) of the desired product in the form of a white-coloured solid is obtained.

Yield: 98%

Spectral characteristics:

¹H NMR (DMSO) δ(ppm): 1.30 (3H, s); 1.40 (3H, s); 1.75 (3H, s); 3.85 (2H, m); 4.15 (2H, m); 4.25 (1H, s, exchangeable with $D_2O$); 4.30 (2H, s); 4.50 (2H, s); 5.15 (1H, s); 5.25 (2H, s); 5.30 (1H, s); 11.10 (1H, s, exchangeable with $D_2O$); 11.18 (1H, s, exchangeable with $D_2O$).

Elemental analysis: (empirical formula: $C_{18}H_{24}Cl_2N_2O_{10}$ M=499.30)

|        | C     | H    | N    | Cl    |
|--------|-------|------|------|-------|
| % found | 43.70 | 4.84 | 5.56 | 14.24 |
| % calc. | 43.30 | 4.94 | 5.61 | 14.20 |

Example 23:
4,5-di-O-Chloroacetylcarbamoyl-1,2-O-isopropylidene-3-(2-methyloxiran-2- yl)-β-D-psicopyranose Following the procedure described for the preparation of Example 4, starting from 0.30 g (0.60 mmol) of the product described in Example 22 and 0.17 g (0.72 mmol) of 72% 3-chloroperbenzoic acid, then purification by chromatography on silica gel (eluant: diethyl ether), 0.19 g (0.38 mmol) of the desired product in the form of a white-coloured foam is obtained.

Yield: 63%

Spectral characteristics:

$^1$H NMR (DMSO) δ(ppm): 1.35 (3H, s); 1.41 (6H, 2s); 2.50 (1H+DMSO, s broad); 2.99 (1H, d); 3.72 (1H, d); 3.85 (1H, s); 4.00 (1H, s, exchangeable with $D_2O$); 4.12 (1H, d); 4.25 (1H, d); 4.40 (2H, s); 4.52 (2H, s); 5.20 (1H, s broad); 5.30 (1H, s broad); 11.06 (1H, s, exchangeable with $D_2O$); 11.20 (1H, s, exchangeable with $D_2O$).

Elemental analysis: (empirical formula: $C_{18}H_{24}Cl_2N_2O_{11}$ M=515.30)

|        | C     | H    | N    | Cl    |
|--------|-------|------|------|-------|
| % found | 41.78 | 4.83 | 5.26 | 14.04 |
| % calc. | 41.96 | 4.69 | 5.44 | 13.76 |

Example 24:
5-O-Phenylcarbamoyl-1,2-O-isopropylidene-3-(2-methyloxiran-2-yl)-4-O-methyl-β-D-psicopyranose The title compound is obtained starting from the compound described in Example 2, in accordance with the procedure described in Example 3, by replacing chloroacetyl isocyanate with phenyl isocyanate and then carrying out the oxidation described in Example 4.

Elemental analysis: (empirical formula: $C_{20}H_{27}NO_8$ M=409.44)

|        | C     | H    | N    |
|--------|-------|------|------|
| % found | 58.95 | 6.39 | 3.48 |
| % calc. | 58.67 | 6.65 | 3.42 |

Example 25:
1,2-O-Isopropylidene-3-isopropenyl-3,4-di-O-methyl-β-D-psicopyranose Step A: 5-O-tert.butyldimethylsilyl-1,2-O-isopropylidene-3-isopropenyl-3,4-di-O-methyl-β-D-psicopyranose 1.24 g (18.21 mmol) of imidazole and 1.92 g (12.73 mmol) of tert.-butyldimethylsilyl chloride are added in succession to a solution, cooled to 0° C., of 2.00 g (7.29 mmol) of the compound obtained in Example 2 in 10 ml of anhydrous N,N-dimethylformamide. The whole is stirred for 72 hours, the temperature being allowed to approach room temperature. The intermediate product is isolated and purified by chromatography on silica gel (eluant: petroleum ether/ethyl acetate, 4:1) to give 2.72 g (7.00 mmol) of the desired compound in the form of a white-coloured solid. A solution of that product (1.18 g; 3.04 mmol) in 5 ml of anhydrous tetrahydrofuran is added to a suspension of sodium hydride (0.22 g; 5.50 mmol) in 6 ml of anhydrous tetrahydrofuran. The whole is stirred under a nitrogen atmosphere at reflux of the solvent for 55 minutes, and 1.15 ml (2.62 g; 18.47 mmol) of methyl iodide are added. The reaction mixture is heated at reflux of the tetrahydrofuran for a further 1.5 hours and then the whole is poured into an aqueous ammonium chloride solution (10%) cooled to 0° C. After customary treatment of the organic phase and purification by chromatography on silica gel (eluant: methylene chloride), 0.86 g (2.14 mmol) of the desired compound in the form of a white-coloured loam is obtained.

Yield: 67%

Spectral characteristics:

$^1$H NMR (DMSO) δ(ppm): 0.10 (6H, s); 0.30 (9H, s); 1.20 (3H, s); 1.30 (3H, s); 1.70 (3H, s); 3.30 (3H, s); 3.35 (3H, s); 3.50 to 3.60 (2H, in); 3.65 (1H, d); 3.70 (1H, d); 4.10 (1H, d); 4.20 (1H, s broad); 5.00 (1H, s broad); 5.20 (1H, s).

Step B: 1,2-O-isopropylidene-3-isopropenyl-3,4-di-O-methyl-β-D-psicopyranose 6.5 ml of a solution (1M in tetrahydrofuran) of tetrabutylanunonium fluoride (6.50 mmol) are added rapidly to a solution, cooled to 0° C., of the compound obtained in the preceding step (0.85 g; 2.11 mmol) in 6 ml of anhydrous tetrahydrofuran. The whole is stirred for 5 hours, the temperature being allowed to approach room temperature. After customary treatment of the organic phase and purification by chromatography on silica gel (eluant: pentane/diethyl ether, 1:1), 0.60 g (2.09 mmol) of the desired compound in the form of a colourless oil is obtained.

Yield: 99%

Spectral characteristics:

$^1$H NMR (DMSO) δ(ppm): 1.30 (3H, s); 1.40 (3H, s); 1.90 (3H, s); 3.30 (3H, s); 3.40 (3H, s); 3.65 to 3.75 (3H, m); 3.80 (1H, dxd); 4.20 (1H, m); 4.30 (2H, m, of which 1 exchangeable with $D_2O$); 5.00 (1H, s broad); 5.30 (1H, s broad).

Example 26:
5-O-Chloroacetylcarbamoyl-1,2-O-isopropylidene-3-isopropenyl-3,4-di-O-methyl-β-D-psicopyranose Following the procedure described for the preparation of Example 3, starting from 0.10 g (0.35 mmol) of the compound obtained in Example 25 and 0.05 ml (0.07 g; 0.59 mmol) of chloroacetyl isocyanate, purification by chromatography on silica gel (eluant: diethyl ether) yields 0.14 g (0.34 mmol) of the desired product in the form of a white-coloured foam.

Yield: 97%

Spectral characteristics:

$^1$H NMR (DMSO) δ(ppm): 1.30 (3H, s); 1.40 (3H, s); 1.90 (3H, s); 3.30 (3H, s); 3.40 (3H, s); 3.75 (1H, d); 3.80 (1H, d); 3.95 (1H, d); 4.00 (1H, d); 4.25 (1H, d); 4.45 (2H, s); 5.05 (1H, s); 5.35 (1H, s); 5.40 (1H, s broad); 11.10 (1H, s, exchangeable with $D_2O$).

Example 27:
1,2-O-Isopropylidene-3,4-di-O-methyl-3-(2-methyloxiran-2-yl)-β-D-psicopyranose Following the procedure described for the preparation of Example 4, starting frown 0.27 g (0.94 mmol) of the product described in Example 25 and 0.81 g (3.38 mmol) of 72% 3-chloroperbenzoic acid, then purification by chromatography on silica gel (eluant: diethyl ether), 0.25 g (0.82 mmol) of the desired product in the form of a white-coloured solid is obtained.

Yield: 87%

Spectral characteristics:

$^1$H NMR (DMSO) δ(ppm): 1.40 (9H, 2s); 2.45 (1H, d); 2.90 (1H, d); 3.35 (6H, 2s); 3.60 (1H, d); 3.65 (1H, dd); 3.85 (1H, d); 3.90 (1H, dd); 4.00 (1H, m); 4.40 (1H, d, exchangeable with D$_2$O); 4.55 (1H, d).

Example 28:
5-O-Chloroacetylcarbamoyl-1,2-O-isopropylidene-3, 4-di-O-methyl-3-(2-methyloxiran-2-yl)-β-D-psicopyranose Following the procedure described for the preparation of Example 3, starting from 0.23 g (0.75 mmol) of the product obtained in Example 27 and 0.08 ml (0.11 g; 0.94 mmol) of chloroacetyl isocyanate, then purification by chromatography on silica gel (eluant: methylene chloride/ethyl acetate, 4:1), 0.25 g (0.59 mmol) of the desired product in the form of a white-coloured foam is obtained.

Yield: 78%

Spectral characteristics:

$^1$H NMR (DMSO) δ(ppm): 1.35 (9H, 2s); 2.50 (1H, d); 2.80 (1H, d); 3.35 (6H, 2s); 3.60 (1H, d); 3.72 (2H, 2d); 4.00 (1H, d); 4.40 (2H, s); 4.55 (1H, d); 5.35 (1H, s broad); 11.02 (1H, s, exchangeable with D$_2$O).

Elemental analysis: (empirical formula: $C_{17}H_{26}ClNO_9$ M=423.85)

|          | C     | H    | N    | Cl   |
|----------|-------|------|------|------|
| % found  | 49.84 | 6.41 | 3.23 | 8.26 |
| % calc.  | 48.17 | 6.18 | 3.30 | 8.37 |

Example 29:
3-Isopropenyl-4,5-di-O-methyl-β-D-psicopyranose

Following the procedure described for the preparation of Example 9, starting from 1.00 g (3.47 mmol) of the compound obtained in Example 14 and 25 g of acidic resin (DOWEX 50X8-100) heated in 50 ml of water, then purification by chromatography on silica gel (eluant: diethyl ether then ethyl acetate), 0.59 g (2.38 mmol) of the desired product in the form of a white-coloured solid is obtained.

Yield: 68%

Spectral characteristics:

$^1$H NMR (DMSO) δ(ppm): 1.75 (3H, s); 3.30 (3H, s); 3.35 (1H, m); 3.52 (3H, s); 3.55 (1H, dd); 3.70 to 3.90 (4H, m); 4.30 (1H, s, exchangeable with D$_2$O); 4.50 (1H, t, exchangeable with D$_2$O); 4.86 (1H, s); 5.10 (1H, s); 5.40 (1H, s, exchangeable with D$_2$O).

Example 30:
1-para-Toluenesulfonyl-3-isopropenyl-4,5-di-O-methyl-β-D-psicopyranose Following the procedure described for the preparation of Example 10, starting from 0.80 g (3.22 mmol) of the compound obtained in Example 29 and 1.53 g of tosyl chloride in 15 ml of anhydrous pyridine, then purification by chromatography on silica gel (eluant: diethyl ether/pentane, 2:1), 0.92 g (2.28 mmol) of the desired product in the form of a white-coloured foam is obtained.

Yield: 70%

Spectral characteristics:

$^1$H NMR (DMSO) δ(ppm): 1.62 (3H, s); 2.40 (3H, s); 3.22 (3H, s); 3.34 (3H, s); 3.68 (1H, d); 3.75–3.85 (3H, m); 3.90 (1H, d); 3.98 (1H, d); 4.40 (1H, s, exchangeable with D$_2$O); 4.81 (1H, s broad); 4.95 (1H, d); 6.46 (1H, s, exchangeable with D$_2$O); 7.45 (2H, d); 7.71 (2H, d).

Example 31:
1-Desoxy-1-iodo-3-isopropenyl-4,5-di-O-methyl-β-D-psicopyranose

Following the procedure described for the preparation of Example 12, starting from 0.10 g (0.25 mmol) of the compound obtained in Example 30 and 0.18 g (1.20 mmol) of sodium iodide in 3 ml of acetone at room temperature, then purification by chromatography on silica gel (eluant: diethyl ether/pentane, 1.5:1), 0.079 g (0.22 mmol) of the desired product in the form of a pale-yellow-coloured solid is obtained.

Yield: 88%

Spectral characteristics:

$^1$H NMR (DMSO) δ(ppm): 1.76 (3H, s); 3.25 (4H, s+d); 3.40 (3H, s); 3.64 (1H, d); 3.75 to 3.95 (4H, m); 4.50 (1H, s, exchangeable with D$_2$O); 4.95 (1H, s broad); 5.15 (1H, s broad); 5.98 (1H, s, exchangeable with D$_2$O).

Example 32:
(3R,6R,7R,8R)-8-Isopropenyl-6,7-dimethoxy-1,4-dioxaspiro[2,5]octan-8-ol 2.20 g (9.49 mmol) of silver(I) oxide are added in portions, over a period of 48 hours, to a solution of the compound obtained in Example 31 (0.52 g; 1.45 mmol) in 5 ml of dioxane. The reaction mixture is then filtered and the filtrate is evaporated to give 0.32 g (1.39 mmol) of the desired product in the form of a white solid.

Yield: 93%

Spectral characteristics:

$^1$H NMR (DMSO) δ(ppm): 1.72 (3H, s); 2.71 (2H, s); 3.40 (6H, 2s); 3.70 (1H, dd); 3.79 to 3.90 (2H, m); 3.95 (1H, dd); 4.70 (1H, s, exchangeable with D$_2$O); 5.00 (1H, s broad); 5.20 (1H, s broad).

Elemental analysis: (empirical formula: $C_{11}H_{18}O_5$ M=230.26)

|          | C     | H    |
|----------|-------|------|
| % found  | 57.20 | 7.89 |
| % calc.  | 57.38 | 7.88 |

Example 33:
5-O-Chloroethylcarbamoyl-1,2-O-isopropylidene-3-isopropenyl-4-O-methyl-β-D-psicopyranose Following the procedure described for the preparation of Example 3, starting from 1.00 g (3.64 mmol) of the compound obtained in Example 2 and 0.46 ml (0.57 g; 5.40 mmol) of chloroethyl isocyanate, 1.35 g (3.55 mmol) of the desired product in the form of a white-coloured solid are obtained.

Yield: 97%

Spectral characteristics:

¹H NMR (DMSO) δ(ppm): 1.30 (3H, s); 1.35 (3H, s); 1.80 (3H, s); 3.25 (3H, s); 3.32 (2H, m); 3.61 (2H, m); 3.72 (1H, d); 3.78 (2H, m); 3.90 (1H, s, exchangeable with $D_2O$); 3.95 (1H, d); 4.12 (1H, d); 5.08 (1H, s); 5.25 (1H, s broad); 5.28 (1H, s broad); 7.75 (1H, t, exchangeable with $D_2O$).

Example 34:
5-O-Chloroethylcarbamoyl-1,2-O-isopropylidene-3-(2-methyloxiran-2-yl)-4-O-methyl-β-D-psicopyranose Following the procedure described for the preparation of Example 4, starting from 0.25 g (0.66 mmol) of the compound obtained in Example 33 and 0.17 g (0.71 mmol) of 72% 3-chloroperbenzoic acid, then purification by chromatography on silica gel (eluant: diethyl ether), 0.16 g (0.40 mmol) of the desired compound in the form of a white-coloured foam is obtained.

Yield: 60%

Spectral characteristics:

¹H NMR (DMSO) δ(ppm): 1.40 (9H, s); 2.42 (1H, d); 2.81 (1H, d); 3.30 (5H, s); 3.60 to 3.75 (4H, m, of which 1H exchangeable with $D_2O$); 3.80 (1H, d); 3.90 (1H, d); 4.20 (1H, d); 5.20 (1H, s broad); 7.60 (1H, t, exchangeable with $D_2O$).

Elemental analysis: (empirical formula: $C_{16}H_{26}ClNO_8$ M=395.84)

|  | C | H | N | Cl |
|---|---|---|---|---|
| % found | 48.34 | 6.43 | 3.68 | 9.27 |
| % calc. | 48.55 | 6.62 | 3.54 | 8.96 |

Example 35:
5-O-(2,4-Difluorophenylcarbamoyl)-1,2-O-isopropylidene-3-isopropenyl-4-O-methyl-β-D-psicopyranose Following the procedure described for the preparation of Example 3, starting from 0.50 g (1.82 mmol) of the compound obtained in Example 2 and 0.43 ml (0.56 g; 3.63 mmol) of 2,4-difluorophenyl isocyanate, then purification by chromatography on silica gel (eluant: pentane/diethyl ether, 4:1), 0.75 g (1.75 mmol) of the desired product in the form of a white-coloured solid is obtained.

Yield: 96%

Spectral characteristics:

¹H NMR (DMSO) δ(ppm): 1.30 (3H, s); 1.40 (3H, s); 1.85 (3H, s); 3.30 (2H, (3H, s); 3.80 s); 3.82 (1H, d); 4.00 (1H, d); 4.10 (1H, s, exchangeable with $D_2O$); 4.15 (1H, d); 5.08 (1H, s broad); 5.30 (1H, s broad); 5.40 (1H, s broad); 7.05 (1H, txd); 7.31 (1H, txd); 7.81 (1H, m); 9.70 (1H, s, exchangeable with $D_2O$).

Example 36:
5-O-(2,4-Difluorophenylcarbamoyl)-1,2-O-isopropylidene-3-(2-methyloxiran-2-yl)-4-O-methyl-β-D-psicopyranose Following the procedure described for the preparation of Example 4, starting from 0.72 g (1.67 mmol) of the compound obtained in Example 35 and 0.45 g (1.88 mmol) of 72% 3-chloroperbenzoic acid, then purification by chromatography on silica gel (eluant: diethyl ether/petroleum ether, 1:1), 0.32 g (0.72 mmol) of the desired compound in the form of a white-coloured foam is obtained.

Yield: 43%

Spectral characteristics:

¹H NMR (DMSO) δ(ppm): 1.40 (9H, s); 2.45 (1H, d); 2.82 (1H, d); 3.36 (3H, s); 3.80 (1H, d); 3.82 (2H, s); 3.95 (1H, s, exchangeable with $D_2O$); 4.00 (1H, d); 4.25 (1H, d); 5.30 (1H, s broad); 7.05 (1H, txd); 7.30 (1H, txd); 7.80 (1H, m); 9.50 (1H, s, exchangeable with $D_2O$).

Elemental analysis: (empirical formula: $C_{20}H_{25}F_2NO_8$ M=445.42)

|  | C | H | N |
|---|---|---|---|
| % found | 53.65 | 5.42 | 3.16 |
| % calc. | 53.93 | 5.66 | 3.14 |

Example 37:
5-O-(3-Trifluoromethylphenylcarbamoyl)-1,2-O-isopropylidene-3-(2-methyloxiran-2-yl)-4-O-methyl-β-D-psicopyranose Following the procedure described for the preparation of Example 3, starting from 0.25 g (0.86 mmol) of the compound obtained in Example 2 and 0.25 ml (0.34 g; 1.82 mmol) of 3-trifluoromethylphenyl isocyanate, then oxidation in accordance with the procedure described in Example 4, and finally purification by chromatography on silica gel (eluant: pentane/ethyl acetate, 4:1), 0.23 g (0.50 mmol) of the desired compound in the form of a white-coloured foam is obtained.

Overall yield: 58%

Spectral characteristics:

¹H NMR (DMSO) δ(ppm): 1.40 (9H, s); 2.45 (1H, d); 2.82 (1H, d); 3.40 (3H, s); 3.60 (1H, s, exchangeable with $D_2O$); 3.80 (3H, d+s); 4.00 (1H, d); 4.25 (1H, d); 5.46 (1H, s broad); 7.32 (1H, d); 7.53 (1H, t); 7.65 (1H, d); 7.92 (1H, s); 10.03 (1H, s, exchangeable with $D_2O$).

Elemental analysis: (empirical formula: $C_{21}H_{26}F_3NO_8$ M=477.43)

|  | C | H | N |
|---|---|---|---|
| % found | 53.33 | 5.34 | 3.17 |
| % calc. | 52.83 | 5.49 | 2.93 |

Example 38:
5-O-(1-Naphthylcarbamoyl)-1,2-O-isopropylidene-3-(2-methyloxiran-2-yl)-4-O-methyl-β-D-psicopyranose Following the procedure described for the preparation of Example 3, starting from 0.25 g (0.86 mmol) of the compound obtained in Example 2 and 0.26 ml (0.30 g; 1.79 mmol) of 1-naphthyl isocyanate, then oxidation in accordance with the procedure described in Example 4, and finally purification by chromatography on silica gel (eluant: methylene chloride/ethyl acetate, 4:1), 0.18 g (0.39 mmol) of the desired compound in the form of a white-coloured solid is obtained.

Overall yield: 45%

Spectral characteristics:

¹H NMR (DMSO) δ(ppm): 1.42 (9H, s); 2.49 (1tt, d); 2.85 (1H, d); 3.40 (3H, s); 3.85 (4H, m, of which 1H exchangeable with $D_2O$); 4.00 (1H, d); 4.26 (1H, d); 5.36 (1H, s broad); 7.45 to 7.60 (3H, m); 7.72 (2H, q); 7.95 (1H, m); 8.15 (1H, m); 9.62 (1H, s, exchangeable with D₂O).

Elemental analysis: (empirical formula: $C_{24}H_{29}NO_8$ M=459.50)

|  | C | H | N |
|---|---|---|---|
| % found | 62.23 | 6.30 | 3.20 |
| % calc. | 62.73 | 6.36 | 3.05 |

Example 39:
1,2-O-Isopropylidene-3-O-allyl-β-D-fructopyranose

Step A: 1,2:4,5-di-O-isopropylidene-3-O-allyl-β-D-fructopyranose 10.00 g (38.42 mmol) of 1,2:4,5-di-O-isopropylidene-β-D-fructopyranose, in solution in 20 ml of anhydrous N,N-dimethylformamide, are added dropwise, at room temperature, to a suspension of sodium hydride (60% in oil; 2.30 g; 57.50 mmol) in 60 ml of anhydrous N,N-dimethylformamide. The reaction mixture is stirred at room temperature for 2 hours, and 6.70 ml (9.37 g; 77.45 mmol) of allyl bromide are added dropwise thereto. After 75 minutes' stirring at room temperature, the reaction mixture is poured into 100 ml of an aqueous ammonium chloride solution (10%) cooled to 0° C. Customary treatment of the organic phase and then purification by chromatography on silica gel (eluant: pentane/diethyl ether, 8:1) yield 9.88 g (32.89 mmol) of the desired product in the form of a yellow-coloured oil.

Yield: 85%

Step B: 1,2-O-isopropylidene-3-O-allyl-β-D-fructopyranose

Following the procedure described for the preparation of Example 1, step C, starting from 9.30 g (30.96 mmol) of the compound obtained in the preceding step, then purification by chromatography on silica gel (eluant: ethyl acetate/diethyl ether, 2:1), 6.04 g (23.20 mmol) of the desired product in the form of a white-coloured solid are obtained.

Yield: 75%

Spectral characteristics:

¹H NMR (DMSO) δ(ppm): 1.30 (3H, s); 1.35 (3H, s); 3.40 (1H, d); 3.50 (1H, d); 3.65 (2H, m); 3.70 (2H, d); 3.90 (1H, d); 4.03 (1H, dxd); 4.35 (1H, dxd); 4.70 (1H, d, exchangeable with D₂O); 4.82 (1H, d, exchangeable with D₂O); 5.10 (1H, d); 5.25 (1H, d); 5.90 (1H, txdxd).

Example 40:
1,2-O-Isopropylidene-3-O-allyl-4-O-methyl-β-D-fructopyranose

Following the procedure described for the preparation of Example 2, starting from 1.00 g (3.84 mmol) of the compound obtained in Example 39 and 1.91 g of dibutyltin (7.67 mmol) at reflux for 48 hours in 30 ml of methanol and then using the intermediate formed in that reaction and subjecting it to the action of 1.20 ml (2.74 g; 19.27 mmol) of methyl iodide at reflux of dioxane (20 ml) for 60 hours, 0.92 g (3.35 mmol) of the desired compound in the form of a white-coloured foam is isolated after chromatography on silica gel (eluant: pentane/ethyl acetate, 2:1).

Yield: 87%

Spectral characteristics:

¹H NMR (DMSO) δ(ppm): 1.28 (3H, s); 1.38 (3H, s); 3.30 (3H, s); 3.32 (1H, dxd); 3.52 (2H, d+s); 3.70 (1H, d); 3.80 (1H, d); 3.92 (2H, m); 4.00 (1H, d); 4.28 (1H, dxd); 4.73 (1H, d, exchangeable with D₂O); 5.10 (1H, d); 5.21 (1H, d); 5.90 (1H, txdxd).

Example 41:
1,2-O-Isopropylidene-3-O-[(2SR)-(2:3-epoxypropyl)]-4-O-methyl-β-D-fructopyranose Following the procedure described for the preparation of Example 4, starting from 1.18 g (4.30 mmol) of the compound obtained in Example 40 and 1.90 g (8.03 mmol) of 72% 3-chloroperbenzoic acid, then purification by chromatography on silica gel (eluant: diethyl ether), 0.53 g (1.82 mmol) of the desired diastereoisomeric mixture is obtained.

Yield: 42% (mixture of the two diastereoisomers)

Spectral characteristics:

¹H NMR (DMSO) δ(ppm): 1.30 (3H, s); 1.40 (3H, s); 2.50 (1H, m); 2.80 (1H, m); 3.10 (1H, m); 3.30 (7H, m); 3.40 (1H, m); 3.70 (2H, m); 3.80 (1H, m); 4.00 (1H, d); 4.70 (1H, d, exchangeable with D₂O).

Example 42:
5-O-Chloroacetylcarbamoyl-1,2-O-isopropylidene-3-[(2S)-(2:3-epoxypropyl)]-4-O-methyl-β-D-fructopyranose and 5-O-Chloroacetylcarbamoyl-1,2-O-isopropylidene-3-[(2R)-(2:3-epoxypropyl)]-4-O-methyl-β-D-fructopyranose

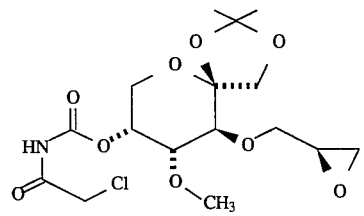

Diastereoisomer A

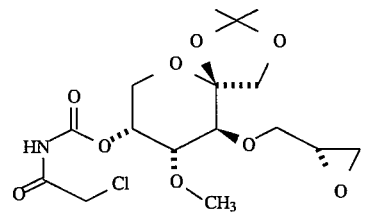

Diastereoisomer B

Following the procedure described for the preparation of Example 3, starting from 0.50 g (1.72 mmol) of the mixture of diastereoisomers obtained in Example 41 and 0.25 ml (0.35 g; 2.93 mmol) of chloroacetyl isocyanate, then purification by chromatography (HPLC, Kromasil 100-5C18 column, eluant: acetonitrile/water, 3:7), 0.189 g (0.46 mmol) of the desired diastereoisomer A and 0.164 g (0.40 mmol) of diastereoisomer B, both in the form of a white-coloured foam, are obtained.

Yield: diastereoisomer A: 27 % diastereoisomer B: 23%

Spectral characteristics Diastereoisomer A:

¹H NMR (DMSO) δ(ppm): 1.32 (3H, s); 1.40 (3H, s); 2.54 (1H, dxd); 2.72 (1H, t); 3.10 (1H, txd); 3.28 (3H, s); 3.29 (1H, m); 3.50 (1H, d); 3.60 (1H, dxd); 3.70 (1H, dxd); 3.85 (2H, d+s); 4.05 (2H, d+s); 4.41 (2H, s); 5.29 (1H, s broad); 11.01 (1H, s, exchangeable with D₂O).

Spectral characteristics Diastereoisomer B:

¹H NMR (DMSO) δ(ppm): 1.32 (3H, s); 1.41 (3H, s); 2.60 (1H, m); 2.70 (1H, m); 3.10 (1H, m); 3.29 (3H, s); 3.50 (1H, d); 3.58 (1H, dxd); 3.70 (1H, dxd); 3.70 to 3.75 (2H, m); 3.80 to 3.85 (2H, m); 4.10 (1H, d); 4.42 (2H, s); 5.25 (1H, s broad); 11.00 (1H, s, exchangeable with D₂O).

Elemental analysis: (empirical formula: $C_{16}H_{24}ClNO_9$ M=409.82)

|  |  | C | H | N | Cl |
|---|---|---|---|---|---|
|  | % calc. | 46.89 | 5.90 | 3.42 | 8.65 |
| Diastereoisomer A | % found | 46.85 | 5.90 | 3.27 | 8.83 |
| Diastereoisomer B | % found | 47.33 | 5.96 | 3.32 | 8.59 |

Example 43:
1,2-O-Isopropylidene-3-(5-methylhex-1-enyl-β-D-psicopyranose

Step A: 1,2:4,5-di-O-isopropylidene-3-(5-methylhex-1-enyl)-β-D-psicopyranose 18 ml of n-butyllithium (2.5 molar in hexane, i.e. 45.00 mmol) are added dropwise, under a nitrogen atmosphere, to a solution, cooled to −78° C., of 6.55 ml of 5-methylhex-1-yne (4.83 g; 50.26 mmol) in 30 ml of anhydrous tetrahydrofuran. The whole is stirred at −78° C. for 15 minutes and then at 0° C. for 30 minutes. The solution is then added dropwise to a solution, cooled to −78° C., of 1,2:4,5-di-O-isopropylidene-β-D-erythro-2,3-hexodiulo-2,6-pyranose (described in Example 1, step A; 6.50 g; 25.17 mmol) in 140 ml of anhydrous toluene. After 2 hours' stirring at −78° C., the reaction mixture is poured into a 10% aqueous ammonium chloride solution (150 ml) cooled to 0° C. Customary treatment of the organic phase yields 8.60 g of 1,2:4,5-di-O-isopropylidene-3-(5-methylhex-1-ynyl)-β-D-psicopyranose in the form of an oily residue, which is used for the following step without being purified. Hydrogenation of a solution of 3.07 g (8.66 mmol) of that compound in 120 ml of benzene in the presence of 0.82 g of Lindlar catalyst for 1.5 hours yields, after filtration, evaporation and chromatography on silica gel (eluant: pentane/ethyl acetate, 20:1), the desired compound (2.41 g; 6.76 mmol) in the form of a colourless oil.

Yield: 75%

Step B: 1,2-O-isopropylidene-3-(5-methylhex-1-enyl)-β-D-psicopyranose

Following the procedure described for the preparation of Example 1 (step C), starting from 2.25 g (6.31 mmol) of the compound obtained in the preceding step, then evaporation of the 25 ml of acetic acid/water mixture, 4:1, 1.98 g (6.26 mmol) of the desired product in the form of a colourless oil are obtained.

Yield: 99%

Spectral characteristics:

$^1$H NMR (DMSO) δ(ppm): 0.85 (6H, d); 1.20 (2H, m); 1.30 (3H, s); 1.40 (3H, s); 1.51 (1H, o); 2.40 (2H, txd); 3.50 (1H, dxd); 3.68 (1H, dxd); 3.81 (3H, m); 4.00 (1H, d); 4.58 (1H, d, exchangeable with D$_2$O); 4.90 (1H, s, exchangeable with D$_2$O); 5.15 (1H, d); 5.45 (1H, m); 5.75 (1H, d, exchangeable with D$_2$O).

Example 44:
1,2-O-Isopropylidene-3-(5-methylhex-1-enyl)-4-O-methyl-β-D-psicopyranose Following the procedure described for the preparation of Example 2, starting from 1.98 g (6.26 mmol) of the compound obtained in Example 43 and 3.15 g of dibutyltin (12.65 mmol) at reflux for 4 hours in 60 ml of methanol, and then using the intermediate formed in that reaction and subjecting it to the action of 6.50 ml (14.82 g; 104.41 mmol) of methyl iodide at reflux of dioxane (50 ml) for 37 hours, and after purification by chromatography on silica gel (eluant: pentane/diethyl ether, 3:1), 1.37 g (4.15 mmol) of the desired compound in the form of a white-coloured foam are obtained.

Yield: 66%

Spectral characteristics:

$^1$H NMR (DMSO) δ(ppm): 0.85 (6H, d); 1.18 (2H, m); 1.30 (3H, s); 1.40 (3H, s); 1.50 (1H, o); 2.40 (2H, m); 3.16 (1H, d); 3.30 (3H, s); 3.72 (1H, dxd); 3.82 (2H, m); 3.95 (1H, d); 4.06 (1H, m); 5.15 (1H, s, exchangeable with D$_2$O); 5.18 (1H, d); 5.45 (1H, m); 5.90 (1H, d, exchangeable with D$_2$O).

Example 45:
1,2-O-Isopropylidene-3-[(2S,3S)-(3-isopentyloxiran-2-yl)]-4-O-methyl-β-D-psicopyranose and
1,2-O-isopropylidene-3-[(2R,3R)-(3-isopentyloxiran-2-yl)]-4-O-methyl-β-D-psicopyranose

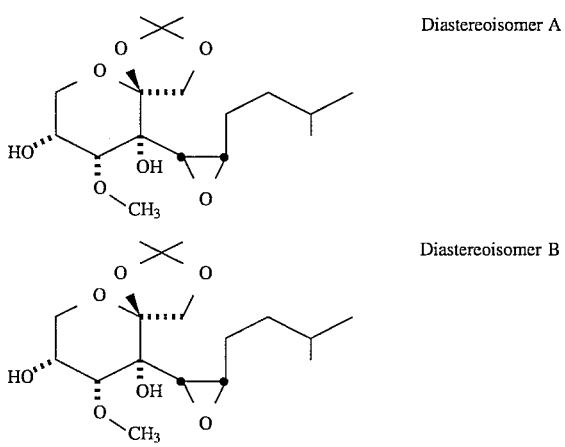

Diastereoisomer A

Diastereoisomer B

Following the procedure described for the preparation of Example 4, starting from 1.31 g (3.96 mmol) of the compound obtained in Example 44 and 1.71 g (7.23 mmol) of 3-chloroperbenzoic acid, then purification by chromatography on silica gel (eluant: diethyl ether/pentane, 2:1), 0.69 g (1.99 mmol) of diastereoisomer A (Rf=0.30) and 0.36 g (1.04 mmol) of diastereoisomer B (Rf=0.10), both in the form of a white-coloured foam, are obtained.

Yield: diastereoisomer A: 50% diastereoisomer B: 26%

Spectral characteristics Diastereoisomer A:

$^1$H NMR (DMSO) δ(ppm): 0.85 (6H, d); 1.28 (2H, m); 1.30 (3H, s); 1.40 (3H, s); 1.55 (1H, o); 1.80 (1H, m); 2.00 (1H, m); 2.80 (1H, txd); 2.90 (1H, d); 3.30 (1H, d); 3.35 (3H, s); 3.72 (1H, d); 3.75 (1H, m); 3.82 (1H, d); 4.10 (1H, s broad); 4.40 (1H, d); 4.96 (1H, s, exchangeable with D$_2$O); 5.93 (1H, d, exchangeable with D$_2$O).

Spectral characteristics Diastereoisomer B:

$^1$H NMR (DMSO) δ(ppm): 0.85 (6H, d); 1.30 (2H, m); 1.30 (3H, s); 1.40 (3H, s); 1.55 (1H, o); 1.66 (1H, m); 1.76 (1H, m); 2.72 (1H, m); 2.90 (1H, d); 3.40 (3H, s); 3.45 (1H, d); 3.70 (1H, dxd); 3.80 (1H, dxd); 3.81 (1H, d); 4.02 (1H, m); 4.10 (1H, d); 4.95 (1H, s, exchangeable with D$_2$O); 5.45 (1H, d, exchangeable with D$_2$O).

Example 46:
5-O-chloroacetylcarbamoyl-1,2-O-isopropylidene-3-[(2S,3S)-(3-isopentyloxiran-2-yl)]-4-O-methyl-β-D-psicopyranose and
5-O-chloroacetylcarbamoyl-1,2-O-isopropylidene-3-[(2R,3R)-(3-isopentyloxiran-2-yl)]-4-O-methyl-β-D-psicopyranose

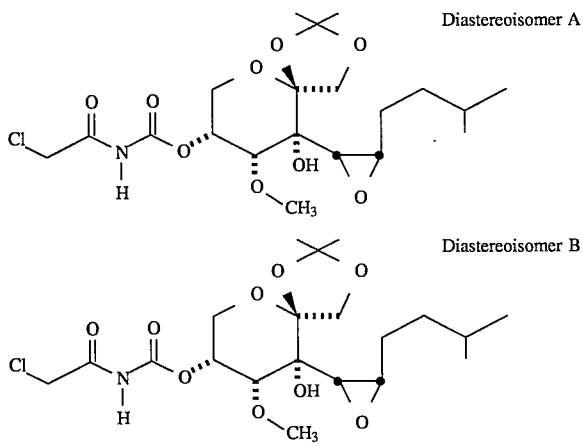

Following the procedure described for the preparation of Example 3, starting from 0.144 g (0.41 mmol) of diastereoisomer A obtained in Example 45 and 0.06 ml (0.08 g; 0.70 mmol) of chloroacetyl isocyanate, then purification by chromatography on silica gel (eluant: diethyl ether/pentane, 1:1), 0.175 g (0.37 mmol) of the desired compound in the form of a white-coloured solid is obtained.

Diastereoisomer B is obtained in accordance with the same procedure starting from diastereoisomer B obtained in Example 45.

Yield: diastereoisomer A: 90% diastereoisomer B: 86%

Spectral characteristics Diastereoisomer A:

$^1$H NMR (DMSO) δ(ppm): 0.85 (6H, d); 1.30 (5H, m); 1.40 (3H, s); 1.55 (1H, o); 1.80 (1H, m); 2.00 (1H, dxdxd); 2.80 (1H, m); 2.95 (1H, d); 3.30 (3H, s); 3.60 (1H, d); 3.80 (1H, d); 3.88 (1H, s, exchangeable with D$_2$O); 3.98 (1H, d); 4.41 (2H, d); 4.50 (2H, s); 5.30 (1H, s broad); 11.10 (1H, s, exchangeable with D$_2$O).

Elemental analysis: (empirical formula: C$_{20}$H$_{32}$ClNO$_9$ M=465.93)

|  |  | C | H | N | Cl |
|---|---|---|---|---|---|
| Diastereoisomer A | % calc. | 51.56 | 6.92 | 3.01 | 7.61 |
|  | % found | 51.22 | 7.01 | 3.04 | 7.97 |
| Diastereoisomer B | % found | 51.47 | 7.00 | 3.03 | 8.27 |

Example 47:
5-O-Ethoxycarbonylcarbamoyl-1,2-O-isopropylidene-3-[(2S*,3S*)-3-isopentyloxiran-2-yl)]-4-O-methyl-β-D-psicopyranose Following the procedure described for the preparation of Example 3, starting from 0.15 g (0.43 mmol) of diastereoisomer A obtained in Example 45 and 0.06 ml (0.08 g; 0.69 mmol) of ethoxycarbonyl isocyanate, then purification by chromatography on silica gel (eluant: pentane/diethyl ether, 1:1), 0.19 g (0.41 mmol) of the desired compound in the form of a white-coloured solid is obtained.

Yield: 95%

Spectral characteristics:

$^1$H NMR (DMSO) δ(ppm): 0.86 (6H, d); 1.20 (3H, t); 1.32 (2H, m); 1.33 (3H, s); 1.35 (3H, s); 1.55 (1H, m); 1.70 to 2.10 (1H, m); 2.80 (1H, m); 2.95 (1H, dd); 3.35 (3H, s); 3.56 (1H, d); 3.76 (2H, m); 3.96 (3H, m, of which 1H exchangeable with D$_2$O); 4.08 (2H, q); 4.43 (1H, d); 5.28 (1H, m); 10.62 (1H, s, exchangeable with D$_2$O).

Elemental analysis: (empirical formula: C$_{21}$H$_{35}$NO$_{10}$ M=461.51)

|  | C | H | N |
|---|---|---|---|
| % found | 54.61 | 7.52 | 2.94 |
| % calc. | 54.65 | 7.64 | 3.03 |

Example 48:
5-O-Ethyloxycarbonylmethyl-1,2-O-isopropynaene-3-[(2S*,3S*)-isopentyloxiran-2-yl]-4-O-methyl-β-D-psicopyranose Following the procedure described for the preparation of Example 3, starting from 0.15 g (0.43 mmol) of diastereoisomer A obtained in Example 45 and 0.06 ml (0.08 g; 0.66 mmol) of ethyl isocyanatoacetate, then purification by chromatography on silica gel (eluant: pentane/diethyl ether, 1:1), 0.17 g (0.36 mmol) of the desired compound in the form of a white-coloured solid is obtained.

Yield: 83%

Spectral characteristics:

$^1$H NMR (DMSO) δ(ppm): 0.88 (6H, d); 1.21 (3H, t); 1.30 (2H, m); 1.35 (3H, s); 1.42 (3H, s); 1.56 (1H, m); 1.80 (1H, m); 1.95 (1H, m); 2.82 (1H, m); 2.98 (1H, d); 3.32 (3H, s); 3.55 (1H, d); 3.68 (2H, dd, of which 1H exchangeable with D$_2$O); 3.80 (3H, m); 3.94 (1H, d); 4.10 (2H, q); 4.43 (1H, d); 5.15 (1H, s broad); 7.95 (1H, t, exchangeable with D$_2$O).

Elemental analysis: (empirical formula: C$_{22}$H$_{37}$NO$_{10}$ M=475.54)

|  | C | H | N |
|---|---|---|---|
| % found | 55.50 | 7.68 | 2.97 |
| % calc. | 55.57 | 7.84 | 2.95 |

Example 49:
5-O-Chloroacetylcarbamoyl-1,2-O-isopropylidene-3-[(2S,3S)-(3-phenylpropyloxiran-2-yl)]-4-O-methyl-β-D-psicopyranose and
5-O-Chloroacetylcarbamoyl-1,2-O-isopropylidene-3-[(2R,3R)-(3-phenylpropyloxiran-2-yl)]-4-O-methyl-β-D-psicopyranose

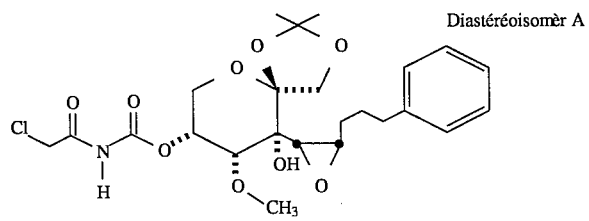

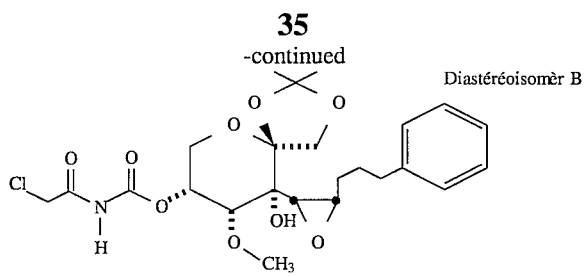

Diastéréoisomèr B

These two diastereoisomers am obtained following the procedures described in Examples 43 to 46, replacing 5-methylhex-1-yne in Example 43 with 5-phenylpent-1-yne.

Spectral characteristics Diastereoisomer A:

$^1$H NMR (DMSO) δ(ppm): 1.35 (3H, s); 1.45 (3H, s); 1.75 (2H, m); 1.90 (1H, m); 2.05 (1H, txd); 2.60 (2H, t); 2.95 (1H, q); 3.00 (1H, s); 3.30 (3H, s); 3.60 (1H, d) 3.80 (2H, m, of which 1 exchangeable with $D_2O$); 3.90 (1H, s); 4.00 (1H, d); 4.50 (3H, m); 5.30 (1H, s broad); 7.30 (5H, m); 11.01 (1H, s, exchangeable with $D_2O$).

Spectral characteristics Diastereoisomer B:

$^1$H NMR (DMSO) δ(ppm): 1.35 (3H, s); 1.45 (3H, s); 1.80 (3H, m); 2.00 (1H, m); 2.65 (2H, t); 2.85 (1H, m); 2.95 (1H, d); 3.35 (3H, s); 3.70 (1H, d); 3.80 (1H, d); 3.85 (1H, s); 4.00 (1H, d); 4.10 (2H, d, of which 1H exchangeable with $D_2$); 4.45 (2H, s); 5.25 (1H, s broad); 7.30 (5H, m); 11.00 (1H, s, exchangeable with $D_2O$).

Elemental analysis: (empirical formula: $C_{24}H_{32}ClNO_9$ M=513.97)

|  |  | C | H | N | Cl |
|---|---|---|---|---|---|
| Diastereoisomer A | % calc. | 56.09 | 6.28 | 2.73 | 6.90 |
|  | % found | 56.44 | 6.29 | 2.73 | 6.84 |
| Diastereoisomer B | % found | 56.55 | 6.49 | 2.53 | 6.78 |

Example 50:
5-O-Chloroacetylcarbamoyl-3-desoxy-1,2-O-isopropylidene-3-(3-phenylpropyloxiran-2-yl)-4-O-methyl-β-D-fructopyranose

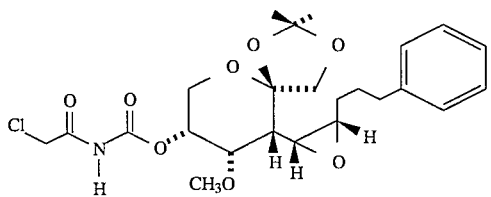

Step A: 1,2:4,5-di-O-isopropylidene-3-methyloxalyl-3-(5-phenylpent-1-yne)-β-D-fructopyranose By replacing 5-methylhex-1-yne in Example 43 with 5-phenylpent-1-yne, the desired 1,2:4,5-di-O-isopropylidene-3-(3-phenylpropyloxiran-2-yl)-β-D-psicopyranose (a single isomer) is obtained in a yield of 88% after chromatography on silica gel (eluant: pentane/diethyl ether, 2:1).

To a solution, cooled to −78° C., of 13.72 g (34.08 mmol) of that compound in 250 ml of anhydrous tetrahydrofuran there are added dropwise, under a nitrogen atmosphere, 44 ml of n-butyllithium (1.6 molar in hexane, i.e. 70.40 mmol). The whole is stirred at −78° C. for 1.5 hours, and 9.20 ml (106.6 mmol) of methyloxalyl chloride are introduced dropwise. The reaction mixture is stirred under a nitrogen atmosphere for 1.75 hours and for 30 minutes at room temperature.

The mixture is then poured into a saturated aqueous sodium hydrogen carbonate solution cooled to 0° C. (250 ml). After customary treatment of the organic phase there are obtained 24 g of an oily residue, which is chromatographed on silica gel (eluant: methylene chloride/ethyl acetate, 99:1) to give 10.44 g (21.38 mmol) of the desired product in the form of a colourless oil.

Yield: 54% (2 steps)

Spectral characteristics:

$^1$H NMR (DMSO) δ(ppm): from 1.10 to 1.50 (12H, 4s); 1.72 (2H, q); 2.28 (2H, t); 2.70 (2H, t); 3.82 (3H, s); 3.90 (2H, m); 4.18 (1H, dd); 4.40 (2H, m); 4.78 (1H, d); 7.20 (3H, m); 7.30 (2H, m).

Step B: 1,2:4,5-di-O-isopropylidene-3-desoxy-3-(5-phenylpent-1-yne)-β-D-fructopyranose 85 mg of 2,2'-azobis-(2-methylpropionitrile) (0.52 mmol) and 1.79 ml (6.65 mmol) of tributyltin hydride are added in succession to a solution of the compound described in step A (2.50 g; 5.11 mmol) in 70 ml of anhydrous toluene. The whole is heated at reflux of the toluene for one hour, and a further 0.25 ml (0.93 mmol) of tributyltin hydride is added. After refluxing for a further one hour, the toluene is evaporated off under reduced pressure and the resulting oily residue is dissolved in 70 ml of diethyl ether. 30 ml of an aqueous potassium fluoride solution (3.6 molar) are added, and then the two phases are separated. After customary treatment of the organic phase there are obtained 4.29 g of an oily residue, which is chromatographed on silica gel (eluant: pentane/ethyl acetate, 15:1) to give 0.62 g (1.60 mmol) of the desired product in the form of a colourless oil.

Yield: 31%

Elemental analysis: (empirical formula: $C_{23}H_{30}O_5$ M=386.49)

|  | C | H |
|---|---|---|
| % found | 71.04 | 7.90 |
| % calc. | 71.48 | 7.82 |

Step C: 5-O-Chloroacetylcarbamoyl-3-desoxy-1,2-O-isopropylidene-3-(3-phenylpropyloxiran-2-yl)-4-O-methyl-β-D-fructopyranose Hydrogenation of a solution of 0.62 g (1.60 mmol) of the compound described in step B in 10 ml of benzene in the presence of 0.29 g of Lindlar catalyst for 45 minutes yields, after filtration and evaporation, the desired compound (0.60 g; 1.54 mmol) in the form of a yellow-coloured oil, which is used for the following step without being purified (crude yield: 96%). Following the experimental protocols described in Examples 1 (step C) to 4, starting from the compound described above, there is obtained 5-O-chloroacetylcarbamoyl-3-dehydroxy-1,2-O-isopropylidene-3-[(5'-phenyl)pentyloxiran-1'-yl]-4-methoxy-β-D-fructopyranose in the form of a white-coloured foam.

Elemental analysis: (empirical formula: $C_{24}H_{32}ClNO_8$ M=497.97)

|  | C | H | N | Cl |
|---|---|---|---|---|
| % found | 57.53 | 6.52 | 2.78 | 7.07 |
| % calc. | 57.89 | 6.48 | 2.81 | 7.12 |

Example 51:
3,5-di-O-Chloroacetylcarbamoyl-1,2-O-isopropylidene-3-(3-phenylpropyloxiran-2-yl)-4-O-methyl-β-D-psicopyranose

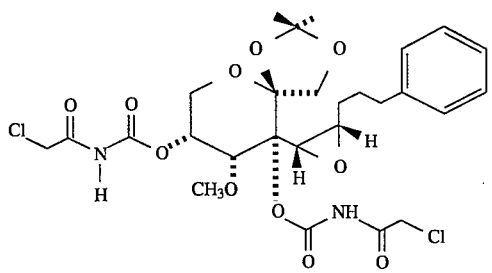

0.50 ml (5.87 mmol) of chloroacetyl isocyanate is added, at room temperature and under a nitrogen atmosphere, to a solution of 0.61 g (1.19 mmol) of diastereoisomer A of Example 49 in 7 ml of anhydrous tetrahydrofuran. The reaction mixture is heated at reflux of the tetrahydrofuran for 20 hours, and a further 0.20 ml of chloroacetyl isocyanate is added. The whole is again refluxed for 24 hours, and then the reaction solution is poured into 5 ml of ice-water. After one hour's stirring and customary treatment of the organic phase there is obtained an oily residue, which is chromatographed on silica gel (eluant: diethyl ether) to give 0.42 g (0.66 mmol) of the desired product in the form of a white-coloured foam.

Yield: 55%

Elemental analysis: (empirical formula: $C_{27}H_{34}Cl_2N_2O_{11}$ M=633.48)

|         | C     | H    | N    | Cl    |
|---------|-------|------|------|-------|
| % found | 51.82 | 5.74 | 4.04 | 10.88 |
| % calc. | 51.19 | 5.41 | 4.42 | 11.19 |

Example 52:
3,5-di-O-Chloroacetylcarbamoyl-1,2-O-isopropylidene-4-O-methyl-3-(5-phenylpentyl)-β-D-psicopyranose

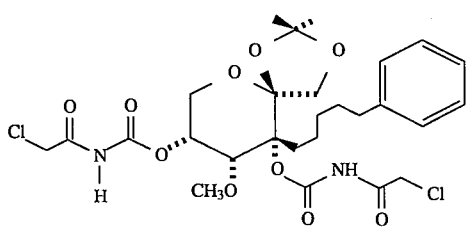

Following the procedure described for the preparation of Examples 43 and 44, replacing 5-methylhex-1-yne with 5-phenylpent-1-yne, the desired 1,2-O-isopropylidene-3-(5-phenylpent-1-enyl)-4-O-methyl-β-D-psicopyranose is obtained. Hydrogenation of 1.97 g (5.23 mmol) of that compound in the presence of 0.90 g of palladium-on-carbon (10%) in 100 ml of ethyl acetate yields 1,2-O-isopropylidene-3-(5-phenylpentyl)-4-O-methyl-β-D-psicopyranose. That compound (0.55 g; 1.44 mmol) is dissolved in 9 ml of methylene chloride in the presence of 0.27 ml (3.17 mmol) of chloroacetyl isocyanate in accordance with the procedure described for the preparation of Example 3. After chromatography on silica gel (eluant: diethyl ether/pentane, 2:1), 0.74 g (1.19 mmol) of the desired product is obtained in the form of a white-coloured foam.

Yield (last step): 82%

Elemental analysis: (empirical formula: $C_{27}H_{36}Cl_2N_2O_{10}$ M=619.50)

|         | C     | H    | N    | Cl    |
|---------|-------|------|------|-------|
| % found | 52.72 | 5.88 | 4.35 | 11.34 |
| % calc. | 52.35 | 5.86 | 4.52 | 11.45 |

Example 53:
3,5-di-O-Chloroacetylcarbamoyl-3-isopropyl-1,2-O-isopropylidene-4-O-methyl-β-D-psicopyranose

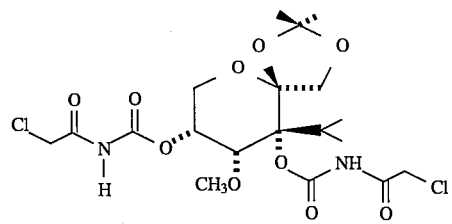

1.00 g of palladium-on-carbon (10%) is added to a solution of 1.35 g (4.92 mmol) of 1,2-O-isopropylidene-3-isopropenyl-4-O-methyl-β-D-psicopyranose (Example 2) in 50 ml of ethyl acetate. The reaction mixture is stirred under a hydrogen atmosphere for 20 hours and is then filtered. After evaporation, the crude product is isolated quantitatively in the form of an oil. That compound (1.35 g; 4.88 mmol) is dissolved in 30 ml of methylene chloride in the presence of 1.25 ml (14.67 mmol) of chloroacetyl isocyanate, in accordance with the procedure described for the preparation of Example 3. After chromatography on silica gel (eluant: pentane/ethyl acetate, 2:1), 1.84 g (3.57 mmol) of the desired product are obtained in the form of a white-coloured foam.

Yield (last step): 73%

Elemental analysis: (empirical formula: $C_{19}H_{28}Cl_2N_2O_{10}$ M=515.34)

|         | C     | H    | N    | Cl    |
|---------|-------|------|------|-------|
| % found | 43.92 | 5.57 | 5.25 | 13.44 |
| % calc. | 44.28 | 5.48 | 5.44 | 13.76 |

Example 54:
3,5-di-O-Chloroacetylcarbamoyl-1,2-O-isopropylidene-3-(2-methyloxiran-2-yl)-4-O-methyl-β-D-fructopyranose

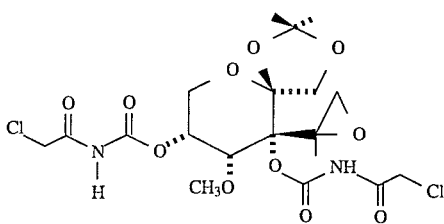

1.55 ml (18.20 mmol) of chloroacetyl isocyanate are added, at room temperature and under a nitrogen atmosphere, to a solution of 1.50 g (3.66 mmol) of the compound described in Example 4 in 15 ml of anhydrous tetrahydrofuran. The reaction mixture is heated at reflux of the tetrahydrofuran for 21 hours, and then the reaction solution is poured into 10 ml of ice-water. After one hour's stirring and customary treatment of the organic phase there is obtained an oily residue, which is subjected to HPLC chromatography on grafted silica gel (RP 18; eluant: acetonitrile/water, 40:60) to give 0.47 g (0.89 mmol) of the desired product in the form of a white-coloured foam.

Yield: 24%

Elemental analysis: (empirical formula: $C_{19}H_{26}Cl_2N_2O_{11}$ M=529.33)

|  | C | H | N | Cl |
|---|---|---|---|---|
| % found | 42.78 | 4.84 | 4.80 | 16.48 |
| % calc. | 42.01 | 4.85 | 5.09 | 16.06 |

Example 55:
1,2-Carbonate-5-O-chloroacetylcarbamoyl-4-methoxy-3-(5-phenylpentyl)-β-D-psicopyranose

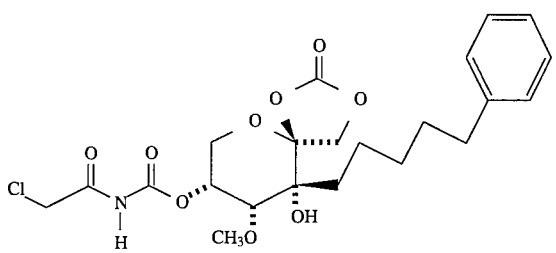

Step A: 1,2-O-isopropylidene-5-O-benzyl-4-O-methyl-3-(5-phenylpent-1-enyl)-β-D-psicopyranose Following the procedure described for the preparation of Examples 43 and 44, replacing 5-methylhex-1-yne with 5-phenylpent-1-yne, the desired 1,2-O-isopropylidene-3-(5-phenylpent-1-enyl) is obtained. To a solution of 2.01 g (5.31 mmol) of that compound in 10 ml of anhydrous tetrahydrofuran there are added at 0° C. 0.28 g of sodium hydride (60% in oil) and 0.20 g (0.54 mmol) of tetrabutylammonium iodide. After 30 minutes' stirring at 0° C., 0.76 ml (6.39 mmol) of benzyl bromide is added and the reaction mixture is stirred at room temperature for 19 hours.

After customary treatment of the organic phase and chromatography on silica gel (eluant: pentane/diethyl ether, 4:1), 2.30 g (4.91 mmol) of the desired compound in the form of a colourless oil are obtained.

Yield: 92%

Spectral characteristics:

$^1$H NMR (DMSO) δ(ppm): 1.28 (3H, s); 1.38 (3H, s); 1.60 (2H, m); 2.40 (2H, m); 2.55 (2H, t); 3.30 (3H, s); 3.39 (1H, s broad); 3.75 (1H, dd); 3.82 (1H, d); 3.95 (1H, dd); 4.00 (1H, d); 4.03 (1H, s broad); 4.48 (1H, s, exchangeable with $D_2O$); 4.61 (1H, d); 4.71 (1H, d); 5.25 (1H, d); 5.52 (1H, m); from 7.10 to 7.40 (10H, m).

Step B: 1,2-carbonate-5-O-benzyl-4-O-methyl-3-(5-phenylpent-1-enyl)-β-D-psicopyranose Following the procedure described for the preparation of Example 9, starting from 1.75 g (3.73 mmol) of the compound described in the preceding step and 18 g of acidic resin (DOWEX 50X8-100) in 60 ml of a tetrahydrofuran/water mixture, 1:1, 1.19 g (2.77 mmol; 74%) of crude product are obtained in the form of a yellow-coloured oil. To a solution of 1.10 g (2.57 mmol) of that compound in 20 ml of anhydrous tetrahydrofuran there are added in portions of 1.50 g, over a period of 72 hours, while heating at reflux, 5.50 g (33.91 mmol) of N,N-carbonyldiimidazole.

The reaction mixture is subsequently diluted with diethyl ether and then washed with a molar solution of hydrochloric acid. The organic phase is subsequently neutralised with sodium hydrogen carbonate and then dried over magnesium sulfate and evaporated. An oily residue is obtained, which is chromatographed on silica gel (eluant: pentane/diethyl ether, 3:1). 0.80 g (1.77 mmol) of the desired compound in the form of a white foam is obtained.

Yield: 51% (2 steps)

Spectral characteristics:

$^1$H NMR (DMSO) δ(ppm): 1.61 (2H, m); 2.40 (2H, m); 2.58 (2H, t); 3.45 (3H, s); 3.55 (1H, s); 3.75 (2H, m); 3.80 (1H, m); 4.22 (1H, d); 4.30 (1H, d); 4.55 (2H, s); 5.15 (1H, d); 5.33 (1H, s, exchangeable with $D_2O$); 5.60 (1H, m); from 7.15 to 7.40 (10H, m).

Step C: 1,2-carbonate-5-O-chloroacetylcarbamoyl-4-O-methyl-3-(5-phenylpentyl)-β-D-psicopyranose 0.40 g of palladium-on-carbon (10%) is added to a solution of 0.70 g (1.55 mmol) of 1,2-carbonate-5-O-benzyl-4-O-methyl-3-(5-phenylpent-1-enyl]-β-D-psicopyranose described in the preceding step in 40 ml of ethyl acetate.

The reaction mixture is stirred under a hydrogen atmosphere for 4 hours and is then filtered. After evaporation, the crude product is isolated quantitatively. That compound (0.48 g; 1.31 mmol) is dissolved in 10 ml of methylene chloride in the presence of 0.39 ml (4.58 mmol) of chloroacetyl isocyanate at 0° C. for 3 hours. After customary treatment of the organic phase and chromatography on silica gel (eluant: heptane/ethyl acetate, 5:2), 0.32 g (0.66 mmol) of the desired compound in the form of a white foam is obtained.

Yield: 50%

Elemental analysis: (empirical formula: $C_{22}H_{28}ClNO_9$ M=485.92)

|  | C | H | N | Cl |
|---|---|---|---|---|
| % found | 54.98 | 5.85 | 2.90 | 7.66 |
| % calc. | 54.38 | 5.81 | 2.88 | 7.30 |

41

Example 56:
1,2-Carbonate-3,5-di-O-chloroacetylcarbamoyl-4-O-methyl-3-(5-phenylpentyl)-β-D-psicopyranose

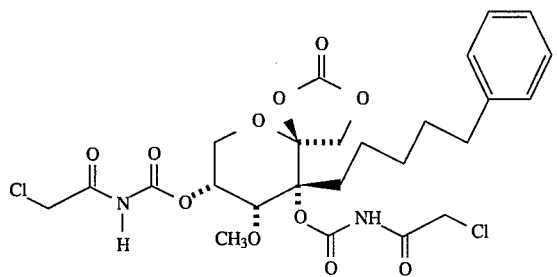

0.13 ml (1.53 mmol) of chloroacetyl isocyanate at room temperature is added to a solution of 1,2-carbonate-5-O-chloroacetylcarbamoyl-4-O-methyl-3-(5-phenylpentyl)-β-D-psicopyranose (0.21 g; 0.43 mmol) in 6 ml of anhydrous methylene chloride. The reaction mixture is stirred under a nitrogen atmosphere for 49 hours.

After customary treatment of the organic phase and chromatography on silica gel (eluant: pentane/ethyl acetate, 1:1), 0.22 g (0.36 mmol) of the desired compound in the form of a white foam is obtained.

Yield: 84%

Elemental analysis: (empirical formula: $C_{25}H_{30}Cl_2N_2O_{11}$ M=605.43)

|          | C     | H    | N    | Cl    |
|----------|-------|------|------|-------|
| % found  | 49.88 | 5.01 | 4.28 | 11.47 |
| % calc.  | 49.60 | 4.99 | 4.63 | 11.71 |

PHARMACOLOGICAL STUDY

Example A: Cytotoxicity of the compounds and of the reference products

Three cell lines were used:
- 1 murine leukaemia, L1210,
- 1 human epidermoid carcinoma, A431,
- 1 primary culture of endothelial cells of pig aorta, ECPA.

The cells are cultured in complete RPMI 1640 culture medium containing 10% foetal calf serum, 2 mM glutamine, 50 units/ml of penicillin, 50 µg/ml of streptomycin and 10 mM HEPES (pH=7.4).

The cells are distributed on microplates and exposed to the cytotoxic compounds. The cells are then incubated for 2 days (L1210), 3 days (ECPA) and 4 days (A431). The number of viable cells is then quantified by means of a colorimetric assay, the Microculture Tetrazolium Assay (Carmichael J., DeGraff W. G., Gazdar A. F., Minna J. D. and Mitchell J. R., Evaluation of a tetrazolium-based semi-automated colorimetric assay: assessment of chemosensitivity testing, Cancer Res., 47, 936–942, (1987)).

The compounds of the present invention exhibited a very considerable cytotoxic effect on the three cell lines.

By way of example, the $IC_{50}$s (concentrations of cytotoxic agent that inhibit the proliferation of the treated cells by 50%) are from 3 to 10 times lower than those of fumagillin, depending upon the cell line.

42

Example B: Inhibition of the neovascularisation of the chorio-allantoid membrane of chicken embryos This test is carried out using chicken embryos as previously described (Crum R., Szabo S. and Folkman J., Science, (1985), 230, 1375–1378). Fertilised eggs (d0) are incubated at 37° C. An air pocket is created by removing 1 ml of albumin (d3), then a window is cut in the shell (d4) and the vitellary membrane is removed in order to tree the chorio-allantoid membrane (CAM). The test products are dissolved in ethanol and placed on methylcellulose disks, which are dried and placed on the CAM 48 hours later (d6). Between 8 and 16 eggs are used per group. The area around the disk is then examined 48 hours later. The eggs exhibiting an avascular area greater than 4 mm in diameter are counted and the results are expressed as the percentage of eggs having an avascular area. The results obtained are shown in the Table below:

| Inhibition of the neovascularisation of the chlorio-allantoid membrane of chicken embryos (dose 125 nM) | |
|---|---|
| Example | % |
| 3 | 59 ± 6 |
| 4 | 84 ± 4 |
| 6 | 51 ± 5 |
| 8 | 55 |
| 13 | 55 ± 3 |
| 17 | 48 ± 12 |
| 20 | 59 ± 6 |
| 22 | 57 ± 12 |
| 42 (Diast. A) | 53 ± 13 |
| 46 (Diast. A) | 68 ± 12 |
| 46 (Diast. B) | 75 ± 13 |
| 49 (Diast. A) | 76 ± 7 |
| 49 (Diast. B) | 79 ± 7 |
| 50 | 75 ± 8 |
| 52 | 88 ± 5 |
| 53 | 95 ± 5 |
| 55 | 90 |
| 56 | 60 |
| Fumagillin | 80 |

Example C: Pharmaceutical composition: tablets

Preparation formula for 1000 tablets containing a dose of 50 mg:

| compound of Example 49 | 50 g |
|---|---|
| wheat starch | 15 g |
| corn starch | 15 g |
| lactose | 65 g |
| magnesium stearate | 2 g |
| silica | 1 g |
| hydroxypropylcellulose | 2 g |

We claim:
1. A compound of formula (I):

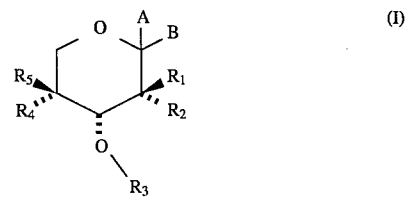

in which:

A - represents —$OR_6$ and B represents —$CH_2$—X,

- or, together with B and the carbon atom carrying them, A forms an oxygen-containing heterocycle selected from the group consisting of oxirane, 2,2-dimethyl[1,3]dioxolane, and [1,3]dioxolan-2-one, $R_1$ represents

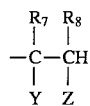

in which Y and Z each represent hydrogen or together form a double bond or together form, with the carbon atoms carrying them, an oxirane ring, and $R_2$ is selected from the group consisting of hydrogen, hydroxy, and —$OR_9$, or $R_1$ represents

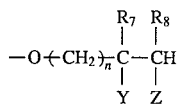

in which n is an integer of 1 to 4 inclusive and Y and Z each represent hydrogen or together form a double bond or together form, with the carbon atoms carrying them, an oxirane ring, and $R_2$ represents hydrogen,

- or $R_1$ represents hydrogen and $R_2$ represents

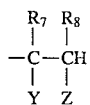

as defined above, $R_3$ is selected the group consisting of hydrogen, linear or branched optionally substituted alkyl having from 1 to 6 carbon atoms inclusive, optionally substituted benzyl, optionally substituted benzoyl, optionally substituted formyl, linear or branched optionally unsaturated and optionally substituted acyl having from 1 to 6 carbon atoms inclusive, allyl, and optionally mono- or di-substituted carbamoyl, $R_4$ - either is selected from the group consisting of hydroxy, linear or branched, optionally substituted alkoxy having 1 to 6 carbon atoms inclusive, optionally mono- or di-substituted carbamoyloxy, piperazinylcarbonyloxy substituted in the 4-position by $R_9$, and imidazol-1-ylcarbonyloxy, and $R_5$ represents hydrogen,

- or, together with $R_5$ and the carbon atom carrying them, forms a carbonyl group, $R_6$, $R_7$ and $R_8$ are selected, each independently of the others, from the group consisting of hydrogen, linear or branched optionally substituted alkyl having 1 to 6 carbon atoms inclusive, and phenylalkyl in which the phenyl group is optionally substituted and the alkyl group, which is linear or branched and is optionally substituted, has 1 to 6 carbon atoms inclusive, $R_9$ is selected from the group consisting of hydrogen, linear or branched optionally substituted alkyl having 1 to 6 carbon atoms inclusive, optionally substituted formyl, linear or branched optionally unsaturated and optionally substituted acyl having 1 to 6 carbon atoms inclusive, linear or branched optionally substituted alkoxycarbonyl having 1 to 6 carbon atoms inclusive, optionally substituted benzyl, and optionally mono- or di-substituted carbamoyl, and X is selected from the group consisting of hydroxy, halogen, optionally substituted phenylsulfonyloxy, and optionally substituted linear or branched alkylsulfonyloxy having 1 to 6 carbon atoms inclusive, its optical or geometrical isomers, in pure form or in the form of a mixture, or its pharmaceutically-acceptable addition salts with an acid, wherein:
- the term "optionally mono- or di-substituted" associated with the above-defined carbamoyl and carbamoyloxy radicals indicates that one or both of the hydrogen atoms carried by the nitrogen atom may be substituted (independently of each other when both hydrogen atoms are substituted) by:
  - linear or branched optionally substituted radical having from 1 to 6 carbon atoms inclusive,
  - optionally substituted formyl,
  - linear or branched, optionally unsaturated and optionally substituted acyl having 1 to 6 carbon atoms inclusive,
  - optionally substituted benzoyl,
  - optionally substituted phenyl,
  - optionally substituted naphthyl, and
  - amino optionally substituted by one or two alkyl having 1 to 6 carbon atoms inclusive in a straight or branched chain, each alkyl being optionally substituted,
- the term "optionally substituted" associated with alkyl, alkoxy, alkoxycarbonyl, formyl, acyl, benzyl, benzoyl, phenyl and naphthyl indicates that those radicals may be substituted by one or more chemical entities selected from hydroxy, halogen, trihalomethyl, amino, alkylamino, dialkylamino, linear or branched alkoxy having 1 to 6 carbon atoms inclusive, linear or branched alkoxycarbonyl having 1 to 6 carbon atoms inclusive, and linear or branched acyl having 1 to 6 carbon atoms inclusive,
- the term "optionally substituted" associated with alkylsulfonyloxy and phenylsulfonyloxy indicates that those radicals may be substituted by one or more linear or branched alkyl having 1 to 6 carbon atoms inclusive, and
- the term "unsaturated acyl" is to be understood as meaning acryloyl or methacryloyl.

2. A compound according to claim 1 in which A and B together form, with the carbon atom carrying them, 2,2-dimethyl[1,3]dioxolane, its optical and geometrical isomers, in pure form or in the form of a mixture, and, its pharmaceutically-acceptable addition salts with an acid.

3. A compound according to claim 1 in which A and B together form, with the carbon atom carrying them, oxirane, its optical and geometrical isomers, in pure form or in the form of a mixture, and, its pharmaceutically-acceptable addition salts with an acid.

4. A compound according to claim 1 which is 5-O-chloroacetylcarbamoyl-1,2-O-isopropylidene-3-(3-phenylpropyloxiran-2-yl)-4-O-methyl-β-D-psicopyranose.

5. A compound according to claim 1 which is 5-O-chloroacetylcarbamoyl-1,2-O-isopropylidene-3-[(2S,3S)-(3-phenylpropyloxiran-2-yl)]-4-O-methyl-β-D-psicopyranose.

6. A compound according to claim 1 which is 5-O-chloroacetylcarbamoyl-1,2-O-isopropylidene-3-[(2R,3R )-(3-phenylpropyloxiran-2-yl)]-4-O-methyl-β-D-psicopyranose.

7. A compound according to claim 1 which is 5-O-chloroacetylcarbamoyl-1,2-O-isopropylidene-3-(2-methyloxiran-2-yl)-4-O-methyl-β-D-psicopyranose, or an optical isomer thereof.

8. A compound according to claim 1 which is 1-bromo-1-desoxy-3-(2-methyloxiran-2yl)-4-O-methyl-5-O-methylcarbamoyl-β-D-psicopyranose, or an optical isomer thereof.

9. A compound according to claim 1 which is 5-O-{1-[4-((2,3,4-trimethoxybenzyl)piperazinyl)]carbonyl }-1,2-O-isopropylidene-3-(2-methyloxiran-2-yl)-4-O-methyl-β-D-psicopyranose, or an optical isomer thereof.

10. A compound according to claim 1 which is 4,5-di-O-chloroacetylcarbamoyl-1,2-O-isopropylidene-3-(2-methyloxiran-2-yl)-β-D-psicopyranose, or an optical isomer thereof.

11. A compound according to claim 1 which is (3R,6R,7R,8R)-8-isopropenyl-6,7-dimethoxy-1,4-dioxaspiro[2,5]octan-8-ol.

12. A compound according to claim 1 which is 5-O-chloroacetylcarbamoyl-1,2-O-isopropylidene-3-(2:3-epoxypropyl)-4-O-methyl-β-D-fructopyranose, or an optical isomer thereof.

13. A compound according to claim 1 which is 5-O-chloroacetylcarbamoyl-1,2-O-isopropylidene-3-(3-isopentyloxiran-2-yl)-4-O-methyl-β-D-psicopyranose, or an optical isomer thereof.

14. A method for treating a mammal afflicted with a disease requiring an angiogenesis inhibitor compising the step of administering to said mammal an amount of a compound of claim 1 which is effective for alleviation of said disease.

15. A pharmaceutical composition useful as an angiogenesis inhibitor comprising an effective amount of a compound of claim 1, together with a pharmaceutically-acceptable excipient.

* * * * *

UNITED STATES PATENT AND TRADEMARK OFFICE
CERTIFICATE OF CORRECTION

PATENT NO. : 5,595,976  Page 1 of 4
DATED : January 21, 1997
INVENTOR(S) : D. Billington; G. Dorey; P. Leon; G. Atassi; A. Pierre; M. Burbridge; N. Guilbaud It is certified that error appears in the above-indentified patent and that said Letters Patent is hereby corrected as shown below:

Column 5, line 7(approx.): In the formula, "$OR_9'$" should read -- $OR'_9$ --.

Column 5, line 60: In the formula, "$OR_3'$" should read -- $OR'_3$ --,

Column 6, line 65: In the formula, "$OR_3'$" should read -- $OR'_3$ --.

Column 7, line 8(approx.): In the formula, "$OR_3'$" should read -- $OR'_3$ --,

Column 7, line 17(approx.): In the formula, "$OR_3'$" should read -- $OR'_3$ --.

Column 10, line 28: In the formula, "$OR_6'$" should read -- $OR'_6$ --.

Column 10, line 45: In the formula, "$OR_6'$" should read -- $OR'_6$ --.

Column 11, line 61: In the formula, "$R_1$" should read -- $R_8$ --.

Column 13, line 26: "-ß-n-erythro-2,3-" should read -- -ß-D-erythro-2,3- --.

Column 24, line 17: "loam" should read -- foam --.

UNITED STATES PATENT AND TRADEMARK OFFICE
CERTIFICATE OF CORRECTION

PATENT NO. : 5,595,976     Page 2 of 4
DATED : January 21, 1997
INVENTOR(S) : D. Billington; G. Dorey; P. Leon; G. Atassi; A. Pierre; M. Burbridge; N. Guilbaud It is certified that error appears in the above-indentified patent and that said Letters Patent is hereby corrected as shown below:

Column 24, line 28: "tylanunonium" at beginning of line should read -- tylammonium --.

Column 27, line 50: Line should read as follows:
-- 1.85(3H,s); 3.30(3H,s); 3.80(2H,s); 3.82(1H,d); 4.00 --.

Column 28, line 65: "2.49(1tt,d);" should read -- 2.49(1H,d); --.

Column 30, line 25: At end of the line, "[(2R" should read -- [(2R) --.

Column 30, line 26: Delete the ")" at the beginning of the line.

Column 34, line 56: At the end of the line, "-2-yl)" should read -- -2-yl)] --.

Column 34, line 57: Delete "]" at the beginning of the line.

Column 35, line 10: The word "am" should read -- are --.

Column 35, line 26: "$D_2$);" at beginning of the line should read -- $D_2O$); --.

Column 42, line 9: The word "tree" should read -- free --.

UNITED STATES PATENT AND TRADEMARK OFFICE
CERTIFICATE OF CORRECTION

PATENT NO. : 5,595,976
DATED : January 21, 1997
INVENTOR(S) : D. Billington; G. Dorey; P. Leon; G. Atassi; A. Pierre; M. Burbridge; N. Guilbaud It is certified that error appears in the above-indentified patent and that said Letters Patent is hereby corrected as shown below:

Column 43, line 38: Insert the word -- from -- between "selected" and "the group".

Column 43, line 39: Delete the word "from".

Column 43, line 43: Delete the word "from".

Column 43, line 46: Delete the word "either".

Column 43, line 47: Delete the "," (comma) after "branched".

Column 44, line 19: Insert -- alkyl -- between "substituted" and "radical".

Column 44, line 20: Delete the word "from" before "1".

Column 44, line 22: Delete the "," (comma) after "branched".

UNITED STATES PATENT AND TRADEMARK OFFICE
CERTIFICATE OF CORRECTION

PATENT NO. : 5,595,976  
DATED : January 21, 1997  
INVENTOR(S) : D. Billington; G. Dorey; P. Leon; G. Atassi; A. Pierre; M. Burbridge; N. Guilbaud Page 4 of 4

It is certified that error appears in the above-indentified patent and that said Letters Patent is hereby corrected as shown below:

Column 44, line 33: Insert a -- , -- (comma) after "phenyl" at the beginning of the line.

Column 44, line 67: Insert ")-" at the end of the line.

Column 45, line 1: Delete ")-" at the beginning of the line.

Column 45, line 8: "-2yl)-" should read -- -2-yl)- --.

Signed and Sealed this

First Day of April, 1997

Attest:

BRUCE LEHMAN

Attesting Officer

Commissioner of Patents and Trademarks